United States Patent
Müller et al.

(10) Patent No.: US 6,441,195 B1
(45) Date of Patent: Aug. 27, 2002

(54) SUBSTITUTED SULPHONYLAMINO(THIO) CARBONYL COMPOUNDS

(75) Inventors: Klaus-Helmut Müller, Düsseldorf; Mark Wilhelm Drewes, Langenfeld; Kurt Findeisen, Leverkusen; Ernst Rudolf F. Gesing, Erkrath-Hochdahl; Johannes R. Jansen; Rolf Kirsten, both of Monheim; Joachim Kluth, Langenfeld; Ulrich Philipp, Köln; Hans-Jochem Riebel, Wuppertal; Markus Dollinger; Hans-Joachim Santel, both of Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/710,079

(22) Filed: Nov. 9, 2000

Related U.S. Application Data

(62) Division of application No. 09/066,385, filed as application No. PCT/EP96/04559 on Oct. 21, 1996, now Pat. No. 6,180,567.

(30) Foreign Application Priority Data

Nov. 2, 1995 (DE) .......................................... 195 40 737

(51) Int. Cl.$^7$ ............................................ C07D 333/26
(52) U.S. Cl. ...................................................... 549/64
(58) Field of Search .............................................. 549/64

(56) References Cited

U.S. PATENT DOCUMENTS

| | | | |
|---|---|---|---|
| 4,877,440 A | 10/1989 | Christensen et al. | |
| 5,057,144 A | 10/1991 | Daum et al. | |
| 5,085,684 A | 2/1992 | Müller et al. | |
| 5,138,072 A | * 8/1992 | Wagner | 549/64 |
| 5,241,074 A | 8/1993 | Daum et al. | |
| 5,252,540 A | 10/1993 | Heistracher et al. | |
| 5,256,632 A | 10/1993 | Wolfe et al. | |
| 5,300,480 A | 4/1994 | Hass et al. | |
| 5,488,028 A | 1/1996 | Haas et al. | |
| 5,534,486 A | 7/1996 | Müller et al. | |

FOREIGN PATENT DOCUMENTS

| | | |
|---|---|---|
| EP | 0 341 489 | 11/1989 |
| EP | 0 431 291 | 6/1991 |
| EP | 0 482 349 | 4/1992 |
| EP | 0 507 171 | 10/1992 |
| EP | 0 534 266 | 3/1993 |
| EP | 0 569 193 | 11/1993 |
| EP | 5 569 810 | 11/1993 |

OTHER PUBLICATIONS

Us Statutory Invention Registration H504, Levitt et al., Aug. 2, 1988.*

* cited by examiner

Primary Examiner—Robert W. Ramsuer
Assistant Examiner—Sonya Wright
(74) Attorney, Agent, or Firm—Norris McLaughlin & Marcus

(57) ABSTRACT

The invention relates to novel substituted sulphonylamino (thio)carbonyl compounds of the formula (I)

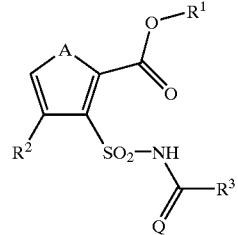

in which
A represents oxygen, sulphur, NH, N-alkyl, N-aryl, —CH=N—, or —N=CH— or —CH=CH—,
Q represents oxygen or sulphur,
$R^1$ represents respectively optionally substituted alkyl, alkenyl, alkinyl, cycloalkyl, cycloalkylalkyl, aryl, arylalkyl, heterocyclyl or heterocyclylalkyl,
$R^2$ represents cyano, nitro, halogen or represents respectively optionally substituted alkyl, alkoxy, alkoxycarbonyl, alkylthio, alkylsulphinyl, alkylsulphonyl, alkenyl, alkinyl, alkenyloxy or alkinyloxy, and
$R^3$ represents respectively optionally substituted heterocyclyl having 5 ring members of which at least one represents oxygen, sulphur or nitrogen and a further one to three may represent nitrogen,
(except for certain individual prior art compounds), furthermore to salts of novel compounds of the formula (I), to various processes and novel intermediates for preparing the novel compounds and to their use as herbicides.

2 Claims, No Drawings

SUBSTITUTED SULPHONYLAMINO(THIO) CARBONYL COMPOUNDS

This application is a division of U.S. Ser. No. 09/066,385, now U.S. Pat. No. 6,180,567 filed on Aug. 7, 1998, which is a 371 of PCT/EP96/04559, filed on Oct. 21, 1996.

The invention relates to novel substituted sulphonylamino(thio)carbonyl compounds, to a plurality of processes and novel intermediates for their preparation and to their use as herbicides.

It is already known that certain sulphonylaminocarbonyl compounds such as, for example, the compounds N-(2-chloro-6-methoxycarbonyl-phenylsulphonyl)-5-phenyl-1,2,4-oxadiazole-3-carboxamide (cf. EP 569810, Example 204), N-(2-chloro-6-methoxycarbonyl-phenylsulphonyl)-oxazole-2-carboxamide (cf. EP 569810, Example 239), N-(2-chloro-6-methoxycarbonyl-phenylsulphonyl)-4-methyl-oxazole-2-carboxamide (cf. EP 569810, Example 278), N-(2-chloro-6-methoxycarbonyl-phenylsulphonyl)-4-ethyl-5-methyl-oxazole-2-carboxamide (cf. EP 569810, Example 329), N-(2-chloro-6-methoxycarbonyl-phenylsulphonyl)-5-ethyl-oxazole-4-carboxamide (cf. EP 569810, Example 366), N-(2-chloro-6-methoxycarbonyl-phenylsulphonyl)-5-ethyl-thiazole-2-carboxamide (cf. EP 569810, Example 441), N-(2-chloro-6-methoxycarbonyl-phenylsulphonyl)-5-methyl-4-methylthio-thiazole-2-carboxamide (cf. EP 569810, Example 532), N-(2-chloro-6-methoxycarbonyl-phenylsulphonyl)-2,5-dimethyl-thiazole-4-carboxamide (cf. EP 569810, Example 576), N-(2-chloro-6-methoxycarbonyl-phenylsulphonyl)-2-chloro-thiazole-5-carboxamide (cf. EP 569810, Example 607), N-(2-chloro-6-methoxy-carbonyl-phenylsulphonyl)-1,3,4-oxadiazole-2-carboxamide (cf. EP 569810, Example 641), N-(2-chloro-6-methoxycarbonyl-phenylsulphonyl)-1,3,4-thiadiazole-2-carboxamide (cf. EP 569810, Example 701), N-(2-chloro-6-methoxycarbonyl-phenylsulphonyl)-5-chloro-1,3,4-thiadiazole-2-carboxamide (cf. EP 569810, Example 735), N-(2-chloro-6-methoxycarbonyl-phenylsulphonyl)-5-phenyl-1,3,4-thiadiazole-2-carboxamide (cf. EP 569810, Example 757), N-(2-chloro-6-methoxy-carbonyl-phenylsulphonyl)-5-methyl-isoxazole-3-carboxamide (cf. EP 569810, Example 791), N-(2-chloro-6-methoxycarbonyl-phenylsulphonyl)-isoxazole-3-carboxamide (cf. EP 569810, Example 861), N-(2-chloro-6-methoxycarbonyl-phenylsulphonyl)-isoxazole-5-carboxamide (cf. EP 569810, Example 871), N-(2-chloro-6-methoxycarbonyl-phenylsulphonyl)-5-methyl-isoxazole-4-carboxamide (cf. EP 569810, Example 918) and N-(2-chloro-6-methoxycarbonyl-phenylsulphonyl)-3,5-dimethyl-isoxazole-4-carboxamide (cf. EP 569810, Example 925) have herbicidal properties (cf. also EP 341489, EP 422469, EP 425948, EP 431291, EP 507171, EP 534266, DE 4029753). However, the activity of these compounds is not satisfactory in every respect.

This invention, accordingly, provides the novel substituted sulphonylamino(thio)carbonyl compounds of the general formula (I),

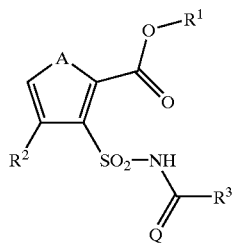

in which

A represents oxygen, sulphur, NH, N-alkyl, N-aryl, —CH=N— or —N=CH—, or —CH=CH—, Q represents oxygen or sulphur, $R^1$ represents respectively optionally substituted alkyl, alkenyl, alkinyl, cycloalkyl, cycloalkylalkyl, aryl, arylalkyl, heterocyclyl or heterocyclylalkyl, $R^2$ represents cyano, nitro, halogen or represents respectively optionally substituted alkyl, alkoxy, alkoxycarbonyl, alkylthio, alkylsulphinyl, alkylsulphonyl, alkenyl, alkinyl, alkenyloxy or alkinyloxy, and $R^3$ represents respectively optionally substituted heterocyclyl having 5 ring members of which at least one represents oxygen, sulphur or nitrogen and a further one to three may represent nitrogen, and salts of compounds of the formula (I), except for the prior art compounds N-(2-chloro-6-methoxycarbonyl-phenylsulphonyl)-5-phenyl-1,2,4-oxadiazole-3-carboxamide (cf. EP 569810, Example 204), N-(2-chloro-6-methoxycarbonyl-phenylsulphonyl)-oxazole-2-carboxamide (cf. EP 569810, Example 239), N-(2-chloro-6-methoxycarbonyl-phenylsulphonyl)-4-methyl-oxazole-2-carboxamide (cf. EP 569810, Example 278), N-(2-chloro-6-methoxycarbonyl-phenylsulphonyl)-4-ethyl-5-methyl-oxazole-2-carboxamide (cf. EP 569810, Example 329), N-(2-chloro-6-methoxycarbonyl-phenylsulphonyl)-5-ethyl-oxazole-4-carboxamide (cf. EP 569810, Example 366), N-(2-chloro-6-methoxycarbonyl-phenylsulphonyl)-5-ethyl-thiazole-2-carboxamide (cf. EP 569810, Example 441), N-(2-chloro-6-methoxycarbonyl-phenylsulphonyl)-5-methyl-4-methylthio-thiazole-2-carboxamide (cf. EP 569810, Example 532), N-(2-chloro-6-methoxycarbonyl-phenylsulphonyl)-2,5-dimethyl-thiazole-4-carboxamide (cf. EP 569810, Example 576), N-(2-chloro-6-methoxycarbonyl-phenylsulphonyl)-2-chloro-thiazole-5-carboxamide (cf. EP 569810, Example 607), N-(2-chloro-6-methoxycarbonyl-phenylsulphonyl)-1,3,4-oxadiazole-2-carboxamide (cf. EP 569810, Example 641), N-(2-chloro-6-methoxycarbonyl-phenylsulphonyl)-1,3,4-thiadiazole-2-carboxamide (cf. EP 569810, Example 701), N-(2-chloro-6-methoxycarbonyl-phenylsulphonyl)-5-chloro-1,3,4-thiadiazole-2-carboxamide (cf. EP 569810, Example 735), N-(2-chloro-6-methoxycarbonyl-phenylsulphonyl)-5-phenyl-1,3,4-thiadiazole-2-carboxamide (cf. EP 569810, Example 757), N-(2-chloro-6-methoxycarbonyl-phenylsulphonyl)-5-methyl-isoxazole-3-carboxamide (cf. EP 569810, Example 791), N-(2-chloro-6-methoxycarbonyl-phenylsulphonyl)-isoxazole-3- carboxamide (cf. EP 569810, Example 861), N-(2-chloro-6-methoxycarbonyl-phenylsulphonyl)-isoxazole-5-carboxamide (cf. EP 569810, Example 871), N-(2-chloro-6-methoxycarbonyl-phenylsulphonyl)-5-methyl-isoxazole-4-carboxamide (cf. EP 569810, Example 918) and N-(2-chloro-6-methoxycarbonyl-phenylsulphonyl)-3,5-dimethyl-isoxazole-4-carboxamide (cf. EP 569810, Example 925) which are excluded by disclaimer.

The novel substituted sulphonylamino(thio)carbonyl compounds of the general formula (I), are obtained when (a) sulphonamides of the general formula (II)

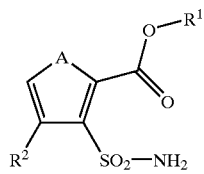

(II)

in which

A, $R^1$ and $R^2$ are each as defined above, are reacted with (thio)carboxylic acid derivatives of the general formula (III)

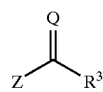

(III)

in which

Q and $R^3$ are each as defined above and

Z represents halogen, alkoxy, aryloxy or arylalkoxy, if appropriate in the presence of an acid acceptor and if appropriate in the presence of a diluent, or when (b) sulphonyl iso(thio)cyanates of the general formula (IV)

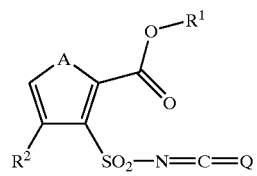

(IV)

in which

A, Q, $R^1$ and $R^2$ are each as defined above, are reacted with heterocycles of the general formula (V)

H—$R^3$  (V)

in which $R^3$ is as defined above, if appropriate in the presence of a reaction auxiliary and if appropriate in the presence of a diluent, or when (c) sulphonyl chlorides of the general formula (VI)

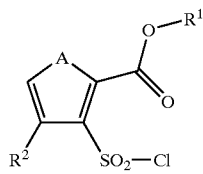

(VI)

in which

A, $R^1$ and $R^2$ are each as defined above, are reacted with heterocycles of the general formula (V)

H—$R^3$  (V)

in which $R^3$ is as defined above, and metal (thio)cyanates of the general formula (VII)

MQCN  (VII)

in which

Q is as defined above, if appropriate in the presence of a reaction auxiliary and if appropriate in the presence of a diluent, or when (d) sulphonyl chlorides of the general formula (VI)

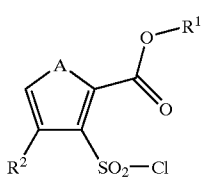

(VI)

in which

A, $R^1$ and $R^2$ are each as defined above, are reacted with (thio)carboxamides of the general formula (VIII)

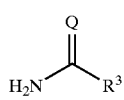

(VIII)

in which

Q and $R^3$ are each as defined above, if appropriate in the presence of an acid acceptor and if appropriate in the presence of a diluent, or when (e) sulphonylamino(thio)carbonyl compounds of the general formula (IX)

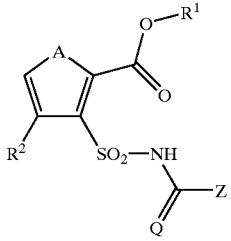

(IX)

in which
A, Q, $R^1$ and $R^2$ are each as defined above and
Z represents halogen, alkoxy, aryloxy or arylalkoxy, are reacted with heterocycles of the general formula (V)

H—$R^3$   (V)

in which
$R^3$ is as defined above,
if appropriate in the presence of an acid acceptor and if appropriate in the presence of a diluent,
and the compounds of the formula (I) obtained by processes (a), (b), (c), (d) or (e) are, if desired, converted into salts by customary methods.

The novel substituted sulphonylamino(thio)carbonyl compounds of the general formula (I) have strong herbicidal activity.

The invention preferably provides compounds of the formula (I) in which

A represents oxygen, sulphur, NH, N—$C_1$–$C_4$-alkyl, N-phenyl, —CH=N— or —N=CH— or —CH=CH—, Q represents oxygen or sulphur, $R^1$ represents optionally cyano-, nitro-, halogen- or $C_1$–$C_4$-alkoxy-substituted $C_1$–$C_6$-alkyl, represents respectively optionally cyano- or halogen-substituted $C_2$–$C_6$-alkenyl or $C_2$–$C_6$-alkinyl, represents respectively optionally cyano-, halogen- or $C_1$–$C_4$-alkyl-substituted $C_3$–$C_6$-cycloalkyl, $C_3$–$C_6$-cycloalkyl-$C_1$–$C_4$-alkyl, represents respectively optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenyl-$C_1$–$C_4$-alkyl, or represents respectively optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted heterocyclyl or heterocyclyl-$C_1$–$C_4$-alkyl, where in each case the heterocyclyl group is selected from the group consisting of oxetanyl, thietanyl, furyl, tetrahydrofuryl, thienyl, tetrahydrothienyl, oxazolyl, isoxazolyl, thiazolyl, oxadiazolyl, thiadiazolyl, $R^2$ represents cyano, nitro, halogen, represents respectively optionally cyano-, halogen- or $C_1$–$C_4$-alkoxy-substituted $C_1$–$C_4$-alkyl, $C_1$–$C_4$-alkoxy, $C_1$–$C_4$-alkoxy-carbonyl, $C_1$–$C_4$-alkylthio, $C_1$–$C_4$-alkylsulphinyl or $C_1$–$C_4$-alkylsulphonyl, or represents respectively optionally cyano- or halogen-substituted $C_2$–$C_4$-alkenyl, $C_2$–$C_4$-alkinyl, $C_2$–$C_4$-alkenyloxy or $C_2$–$C_4$-alkinyloxy, and $R^3$ represents respectively optionally substituted heterocyclyl of the formulae below,

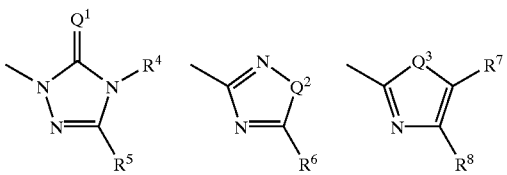

in which
$Q^1$, $Q^2$ and $Q^3$ each represent oxygen or sulphur and
$R^4$ represents hydrogen, hydroxyl, amino, cyano, represents $C_2$–$C_{10}$-alkylideneamino, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbony-substituted $C_1$–$C_6$-alkyl, represents respectively optionally fluorine-, chlorine- and/or bromine-substituted $C_2$–$C_6$-alkenyl or $C_2$–$C_6$-alkinyl, represents respectively optionally fluorine-, chlorine-, bromine-, cyano-, $C_1$–$C_4$-alkoxy- or $C_1$–$C_4$-alkoxy-carbonyl-substituted $C_1$–$C_6$-alkoxy, $C_1$–$C_6$-alkylamino or $C_1$–$C_6$-alkyl-carbonyl-amino, represents $C_3$–$C_6$-alkenyloxy, represents di-($C_1$–$C_4$-alkyl)-amino, represents respectively optionally fluorine-, chlorine-, bromine-, cyano- and/or $C_1$–$C_4$-alkyl-substituted $C_3$–$C_6$-cycloalkyl, $C_3$–$C_6$-cycloalkyl-amino or $C_3$–$C_6$-cycloalkyl-$C_1$–$C_4$-alkyl, or represents respectively optionally fluorine-, chlorine-, bromine-, cyano-, nitro-, $C_1$–$C_4$-alkyl-, trifluoromethyl- and/or $C_1$–$C_4$-alkoxy-substituted phenyl or phenyl-$C_1$–$C_4$-alkyl, $R^5$ represents hydrogen, hydroxyl, mercapto, amino, cyano, fluorine, chlorine, bromine, iodine, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents respectively optionally fluorine-, chlorine- and/or bromine-substituted $C_2$–$C_6$-alkenyl or $C_2$–$C_6$-alkinyl, represents respectively optionally fluorine-, chlorine-, cyano-, $C_1$–$C_4$-alkoxy- or $C_1$–$C_4$-alkoxy-carbonyl-substituted $C_1$–$C_6$-alkoxy, $C_1$–$C_6$-alkylthio, $C_1$–$C_6$-alkylamino or $C_1$–$C_6$-alkyl-carbonylamino, represents $C_3$–$C_6$-alkenyloxy, $C_3$–$C_6$-alkinyloxy, $C_3$–$C_6$-alkenylthio, $C_3$–$C_6$-alkinylthio, $C_3$–$C_6$-alkenylamino or $C_3$–$C_6$-alkinylamino, represents di-($C_1$–$C_4$-alkyl)-amino, represents respectively optionally methyl- and/or ethyl-substituted aziridino, pyrrolidino, piperidino or morpholino, represents respectively optionally fluorine-, chlorine-, bromine-, cyano- and/or $C_1$–$C_4$-alkyl-substituted $C_3$–$C_6$-cycloalkyl, $C_5$–$C_6$-cycloalkenyl, $C_3$–$C_6$-cycloalkyloxy, $C_3$–$C_6$-cycloalkylthio, $C_3$–$C_6$-cycloalkylamino, $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio or $C_3$–$C_6$-cycloalkyl-$C_1$–$C_4$-alkylamino, or represents respectively optionally fluorine-, chlorine-, bromine-, cyano-, nitro-, $C_1$–$C_4$-alkyl-, trifluoromethyl-, $C_1$–$C_4$-alkoxy- and/or $C_1$–$C_4$-alkoxy-carbony-substituted phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, or $R^4$ and $R^5$ together represent optionally branched alkanediyl having 3 to 11 carbon atoms, furthermore $R^6$, $R^7$ and $R^8$ are identical or different and each represents hydrogen, cyano, fluorine, chlorine, bromine, or represents respectively optionally fluorine-, chlorine-, bromine- or $C_1$–$C_4$-alkoxy-substituted alkyl, alkenyl, alkinyl, alkoxy, alkenyloxy, alkinyloxy, alkylthio, alkenylthio, alkinylthio, alkylsulphinyl or alkylsulphonyl having in each case up to 6 carbon atoms or represent optionally cyano-, fluorine-, chlorine-, bromine- or $C_1$–$C_4$-alkyl-substituted cycloalkyl having 3 to 6 carbon atoms, except for the prior art compounds N-(2-chloro-6-methoxycarbonyl-phenylsulphonyl)-5-phenyl-1,2,4-oxadiazole-3-carboxamide (cf. EP 569810, Example 204), N-(2-chloro-6-methoxycarbonyl-phenylsulphonyl)-oxazole-2-carboxamide (cf. EP 569810, Example 239), N-(2-chloro-6-methoxycarbonyl-phenylsulphonyl)-4-methyl-oxazole-2-carboxamide (cf. EP 569810, Example 278), N-(2-chloro-6-methoxycarbonyl-phenylsulphonyl)-4-ethyl-5-methyl-oxazole-2-carboxamide (cf. EP 569810, Example 329), N-(2-chloro-6-methoxycarbonyl-phenylsulphonyl)-5-ethyl-oxazole-4-carboxamide (cf. EP 569810, Example 366), N-(2-chloro-6-methoxycarbonyl-phenylsulphonyl)-5-ethyl-thiazole-2-carboxamide (cf. EP 569810, Example 441), N-(2-chloro-6-methoxycarbonyl-phenylsulphonyl)-5-methyl-4-methylthio-thiazole-2-carboxamide (cf. EP 569810, Example 532), N-(2-chloro-6-methoxycarbonyl-phenylsulphonyl)-2,5-dimethyl-thiazole-4-carboxamide (cf. EP 569810, Example 576), N-(2-chloro-6-methoxycarbonyl-phenylsulphonyl)-2-chloro-thiazole-5-carboxamide (cf. EP 569810, Example 607), N-(2-chloro-6-methoxycarbonyl-phenylsulphonyl)-1,3,4-oxadiazole-2-carboxamide (cf. EP 569810, Example 641), N-(2-chloro-6-methoxycarbonyl-phenylsulphonyl)-1,3,4-thiadiazole-2-carboxamide (cf. EP 569810, Example 701), N-(2-chloro-6-methoxycarbonyl-phenylsulphonyl)-5-chloro-1,3,4-thiadiazole-2-carboxamide (cf. EP 569810, Example 735), N-(2-chloro-6-methoxycarbonyl-phenylsulphonyl)-5-phenyl-1,3,4-thiadiazole-2-carboxamide (cf. EP 569810, Example 757), N-(2-chloro-6-methoxycarbonyl-phenylsulphonyl)-5-methyl-isoxazole-3-carboxamide (cf. EP 569810, Example 791), N-(2-chloro-6-methoxycarbonyl-phenylsulphonyl)-isoxazole-3-carboxamide (cf. EP 569810, Example 861), N-(2-chloro-6-methoxycarbonyl-phenylsulphonyl)-isoxazole-5-carboxamide (cf. EP 569810, Example 871), N-(2-chloro-6-methoxycarbonyl-phenylsulphonyl)-5-methyl-isoxazole-4-carboxamide (cf. EP 569810, Example 918) and N-(2-chloro-6-methoxycarbonyl-phenylsulphonyl)-3,5-dimethyl-isoxazole4-carboxamide (cf. EP 569810, Example 925) which are excluded by disclaimer.

The invention furthermore preferably provides the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which A, Q, $R^1$, $R^2$ and $R^3$ are each preferably as defined above.

The invention in particular provides compounds of the formula (I), in which

A represents sulphur, N-methyl, —CH=N— or —N=CH— or —CH=CH—,

Q represents oxygen or sulphur, $R^1$ represents respectively optionally cyano-, fluorine-, chlorine-, methoxy- or ethoxy-substituted methyl, ethyl, n- or i-propyl, n-, i- or s-butyl, represents respectively optionally cyano-, fluorine- or chlorine-substituted propenyl, butenyl, propinyl or butinyl, represents respectively optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclo-hexylmethyl, represents respectively optionally cyano-, fluorine-, chlorine-, bromine-, methyl-, ethyl-, trifluoromethyl-, methoxy-, ethoxy-, difluoromethoxy- or trifluoromethoxy-substituted phenyl, phenylmethyl or phenylethyl, or represents respectively optionally cyano-, fluorine-, chlorine-, bromine-, methyl-, ethyl-, methoxy- or ethoxy-substituted heterocyclyl or heterocyclyl-methyl, where in each case the heterocyclyl group is selected from the group consisting of oxetanyl, thietanyl, furyl, tetrahydrofuryl, thienyl, tetrahydrothienyl, $R^2$ represents cyano, fluorine, chlorine, bromine, represents respectively optionally cyano-, fluorine-, chlorine-, methoxy- or ethoxy-substituted methyl, ethyl, n- or i-propyl, n-, i- or s-butyl, methoxy, ethoxy, n- or i-propoxy, methoxycarbonyl, ethoxycarbonyl, n- or i-propoxycarbonyl, methylthio, ethylthio, methylsulphinyl, ethylsulphinyl, methylsulphonyl or ethylsulphonyl, or represents respectively optionally cyano-, fluorine- or chlorine-substituted propenyl, butenyl, propinyl, butinyl, propenyloxy or propinyloxy, and $R^3$ represents respectively optionally substituted heterocyclyl of the formulae below,

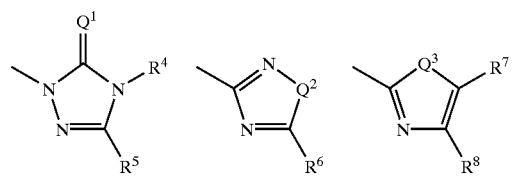

in which $Q^1$, $Q^2$ and $Q^3$ each represent oxygen or sulphur and $R^4$ represents hydrogen, hydroxyl, amino, represents respectively optionally fluorine-, chlorine-, cyano-, methoxy- or ethoxy-substituted methyl, ethyl, n- or i-propyl, n-, i-, s- or t-butyl, represents respectively optionally fluorine-, chlorine- or bromine-substituted propenyl, butenyl, propinyl or butinyl, represents respectively optionally fluorine-, chlorine-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, represents propenyloxy or butenyloxy, represents dimethylamino or diethylamino, represents respectively optionally fluorine-, chlorine-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents respectively optionally fluorine-, chlorine-, methyl-, trifluoromethyl- and/or methoxy-substituted phenyl or benzyl, $R^5$ represents hydrogen, hydroxyl, mercapto, amino, fluorine, chlorine, bromine, represents respectively optionally fluorine-, chlorine-, cyano-, methoxy- or ethoxy-substituted methyl, ethyl, n- or i-propyl, n-, i-, s- or t-butyl, represents respectively optionally fluorine-, chlorine- or bromine-substituted ethenyl, propenyl, butenyl, propinyl or butinyl, represents respectively optionally fluorine-, chlorine-, cyano-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, represents propenyloxy, butenyloxy, propinyloxy, butinyloxy, propenylthio, propadienylthio butenylthio, propinylthio, butinylthio, propenylamino, butenylamino, propinylamino or butinylamino, represents dimethylamino, diethylamino or dipropylamino, represents respectively optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents respectively optionally fluorine-, chlorine-, methyl-, trifluoromethyl-, methoxy- and/or methoxycarbonyl-substituted phenyl, benzyl, phenoxy, benzyloxy, phenylthio, benzylthio, phenylamino or benzylamino, or $R^4$ and $R^5$ together represent optionally branched alkanediyl having 3 to 11 carbon atoms, furthermore $R^6$, $R^7$ and $R^8$ are identical or different and each represents hydrogen, cyano, fluorine, chlorine, bromine, or represents respectively optionally fluorine-, chlorine-, methoxy- or ethoxy-substituted methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylsulphinyl, ethylsulphinyl, methylsulphonyl or ethylsulphonyl, or represents cyclopropyl, except for the prior art compounds N-(2-chloro-6-methoxycarbonyl-phenylsulphonyl)-5-phenyl-1,2,4-oxadiazole-3-carboxamide (cf. EP 569810, Example 204), N-(2-chloro-6-methoxycarbonyl-phenylsulphonyl)-oxazole-2-carboxamide (cf. EP 569810, Example 239), N-(2-chloro-6-methoxycarbonyl-phenylsulphonyl)-4-methyl-oxazole-2-carboxamide (cf. EP 569810, Example 278), N-(2-chloro-6-methoxycarbonyl-phenylsulphonyl)-4-ethyl-5-methyl-oxazole-2-carboxamide (cf. EP 569810, Example 329), N-(2-chloro-6-methoxycarbonyl-phenylsulphonyl)-5-ethyl-oxazole-4-carboxamide (cf EP 569810, Example 366), N-(2-chloro-6-methoxycarbonyl-phenylsulphonyl)-5-ethyl-thiazole-2-carboxamide (cf. EP 569810, Example 441), N-(2-chloro-6-methoxycarbonyl-phenylsulphonyl)-5-methyl-4-methylthio-thiazole-2-carboxamide (cf EP 569810, Example 532), N-(2-chloro-6-methoxycarbonyl-phenylsulphonyl)-2,5-dimethyl-thiazole-4-carboxamide (cf. EP 569810, Example 576), N-(2-chloro-6-methoxycarbonyl-phenylsulphonyl)-2-chloro-thiazole-5-carboxamide (cf. EP 569810, Example 607), N-(2-chloro-6-methoxycarbonyl-phenylsulphonyl)-1,3,4-oxadiazole-2-carboxamide (cf. EP 569810, Example 641), N-(2-chloro-6-methoxycarbonyl-phenylsulphonyl)-1,3,4-thiadiazole-2-carboxamide (cf. EP 569810, Example 701), N-(2-chloro-6-methoxycarbonyl-phenylsulphonyl)-5-chloro-1,3,4-thiadiazole-2-carboxamide (cf. EP 569810, Example 735), N-(2-chloro-6-methoxycarbonyl-phenylsulphonyl)-5-phenyl-1,3,4-thiadiazole-2-carboxamide (cf. EP 569810, Example 757), N-(2-chloro-6-methoxycarbonyl-phenylsulphonyl)-5-methyl-isoxazole-3-carboxamide (cf. EP 569810, Example 791), N-(2-chloro-6-methoxycarbonyl-phenylsulphonyl)-isoxazole-3-carboxamide (cf. EP 569810, Example 861), N-(2-chloro-6-methoxycarbonyl-phenylsulphonyl)-isoxazole-5-carboxamide (cf. EP 569810, Example 871), N-(2-chloro-6-methoxycarbonyl-phenylsulphonyl)-5-methyl-isoxazole-4-carboxamide (cf EP 569810, Example 918) and N-(2-chloro-6-methoxycarbonyl-phenylsulphonyl)-3,5-dimethyl-isoxazole-4-carboxamide (cf. EP 569810, Example 925) which are excluded by disclaimer.

A very particularly preferred group of compounds according to the invention are the compounds of the formula (I) in which A represents sulphur or —CH=CH—, Q represents oxygen or sulphur, $R^1$ represents methyl, ethyl, n- or i-propyl, 2-cyano-ethyl, 2-fluoro-ethyl, 2,2-difluoro-ethyl, 2,2,2-trifluoro-ethyl, 2-chloro-ethyl, 2,2-dichloro-ethyl, 2,2,2-trichloro-ethyl, 2-methoxy-ethyl, 2-ethoxy-ethyl or oxetanyl, $R^2$ represents fluorine, chlorine, bromine, methyl, ethyl, n- or i-propyl, n-, i- or s-butyl, trifluoromethyl, methoxy, ethoxy, n- or i-propoxy, difluoromethoxy, trifluoromethoxy or trifluoroethoxy, and $R^3$ represents optionally substituted triazolinyl of the formula below

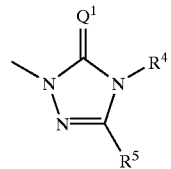

in which $Q^1$ represents oxygen or sulphur and $R^4$ represents respectively optionally fluorine-, chlorine-, methoxy- or ethoxy-substituted methyl, ethyl, n- or i-propyl, represents respectively optionally fluorine- or chlorine-subsituted propenyl or propinyl, represents methoxy, ethoxy, n- or i-propoxy, methylamino, ethylamino, n- or i-propylamino, represents propenyloxy, represents dimethylamino or represents cyclopropyl, $R^5$ represents chlorine or bromine, represents respectively optionally fluorine-, chlorine-, cyano-, methoxy- or ethoxy-substituted methyl, ethyl, n- or i-propyl, n-, i-, s- or t-butyl, represents respectively optionally fluorine-, chlorine- or bromine-substituted ethenyl, propenyl, butenyl, propinyl or butinyl, represents respectively optionally fluorine-, chlorine-, cyano-, methoxy- or ethoxy-subsituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, represents propenyloxy, butenyloxy, propinyloxy, butinyloxy, propenylthio, propadienylthio, butenylthio, propinylthio, butinylthio, propenylamino, butenylamino, propinylamino or butinylamino, represents dimethylamino, diethylamino or dipropylamino, represents respectively optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents respectively optionally fluorine-, chlorine-, methyl-, trifluoromethyl-, methoxy- and/or methoxycarbonyl-substituted phenyl, benzyl, phenoxy, benzyloxy, phenylthio, benzylthio, phenylamino or benzylamino, or $R^4$ and $R^5$ together represent optionally branched alkanediyl having 3 to 11 carbon atoms.

The radical definitions listed above, whether general or listed in ranges of preference, apply both to the end products of the formula (I) and, correspondingly, to the starting materials and/or intermediates required in each case for the preparation. These radical definitions can be combined as desired with one another, thus including combinations between the preferred ranges indicated.

Using, for example, 2-fluoro-6-methoxycarbonyl-benzenesulphonamide and 5-ethoxy-4-methyl-2-phenoxycarbonyl-2,4-dihydro-3H-1,2,4-triazole-3-thione as starting materials, the course of the reaction in the process (a) according to the invention can be illustrated by the following equation:

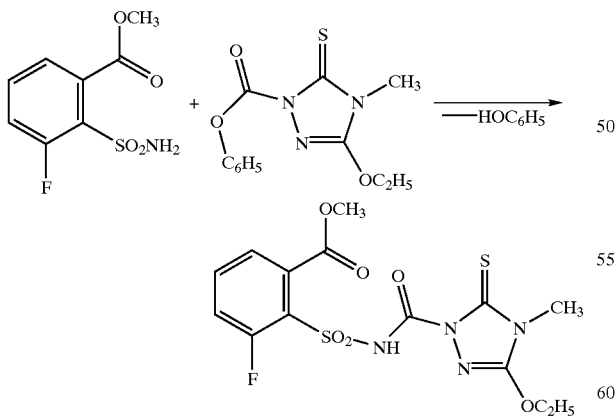

Using, for example, 4-chloro-2-ethoxycarbonyl-3-thienylsulphonyl isothiocyanate and 5-ethyl-4-methoxy-2,4-dihydro-3H-1,2,4-triazol-3-one as starting materials, the course of the reaction in the process (b) according to the invention can be illustrated by the following equation:

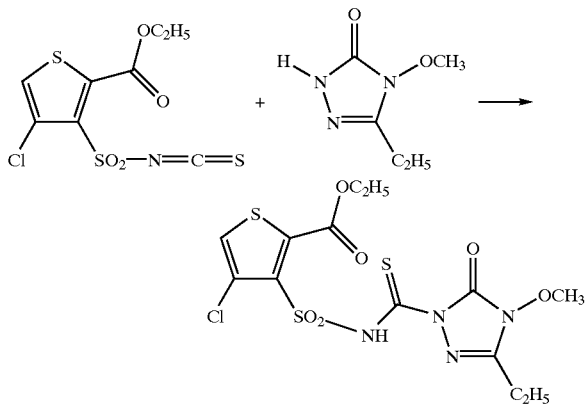

Using, for example, 2-methoxycarbonyl-6-methyl-benzenesulphonyl chloride, 5-ethylthio-4-methoxy-2,4-dihydro-3H-1,2,4-triazol-3-one and potassium cyanate as starting materials, the course of the reaction in the process (c) according to the invention can be illustrated by the following equation:

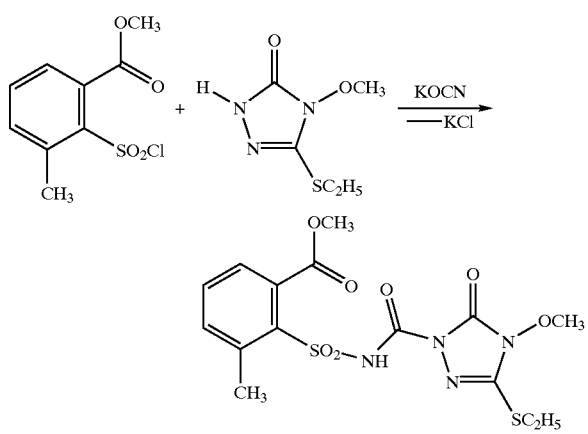

Using, for example, 2-ethoxycarbonyl-6-trifluoromethyl-benzenesulphonyl chloride and 5-methyl-1,2,4-oxadiazole-3-carboxamide as starting materials, the course of the reaction in the process (d) according to the invention can be illustrated by the following equation:

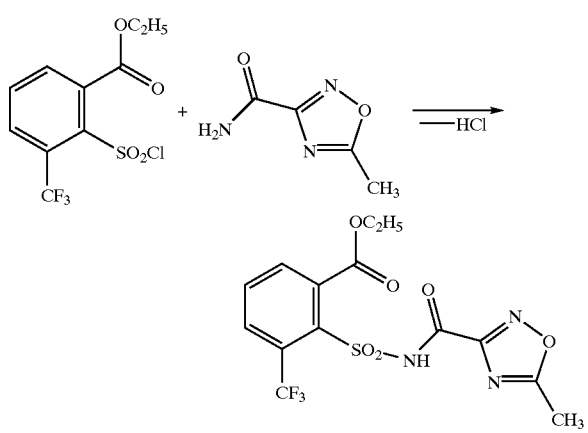

Using, for example, N-(2-chloro-6-methoxycarbonyl-phenylsulphonyl)-O-methyl-urethane and 4-methyl-5- methylthio-2,4-dihydro-3H-1,2,4-triazol-3-one as starting materials, the course of the reaction in the process (e) according to the invention can be illustrated by the following equation:

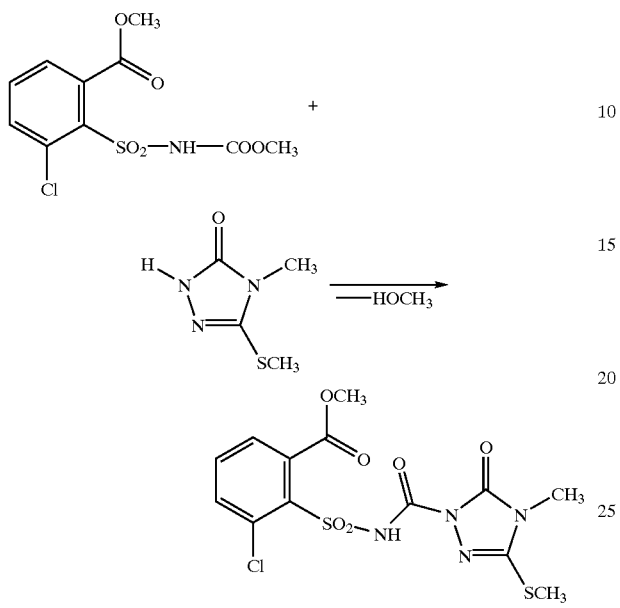

A general definition of the sulphonamides to be used as starting materials in the process (a) according to the invention for preparing the compounds of the formula (I) is given by the formula (II). In the formula (II), A, $R^1$ and $R^2$ each preferably or in particular have that meaning which has already been indicated above in connection with the description of the compounds of the formula (I) according to the invention as being preferable or, respectively, particularly preferable for A, $R^1$ and $R^2$.

The starting materials of the formula (II) are known and/or can be prepared by processes known per se (cf. U.S. Pat. Nos. 4,546,179, 5,084,086, 5,157,119, WO 8909214, WO9115478).

The sulphonamides of the general formula (IIa)

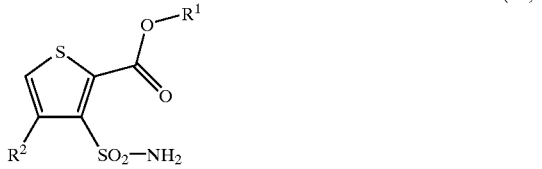

(IIa)

in which $R^1$ and $R^2$ are each as defined above have not yet been disclosed in the literature and, as novel compounds, form part of the subject-matter of the present application.

The novels sulphonamides of the formula (IIa) are obtained when sulphonyl chlorides of the formula (VIa)

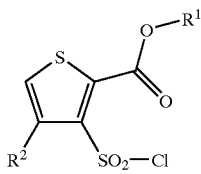

(VIa)

in which $R^1$ and $R^2$ are each as defined above, are reacted with ammonia, if appropriate in the presence of a diluent such as, for example, water, at temperatures between 0° C. and 50° C. (cf. the Preparation Examples).

The sulphonyl chlorides of the formula (VIa) have not yet been disclosed in the literature; as novel compounds, they also form part of the subject-matter of the present application.

The novel sulphonyl chlorides of the formula (VIa) are obtained when corresponding amino compounds of the general formula (X)

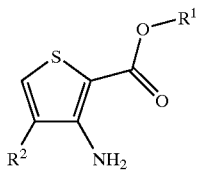

(X)

in which $R^1$ and $R^2$ are each as defined above, are reacted with an alkali metal nitrite such as, for example, sodium nitrite, in the presence of hydrochloric acid at temperatures between −10° C. and +10° C. and the resulting diazonium salt solution is reacted with sulphur dioxide in the presence of a diluent such as, for example, dichloromethane, 1,2-dichloro-ethane or acetic acid, and in the presence of a catalyst such as, for example, copper(I) chloride and/or copper(II) chloride, at temperatures between −10° C. and +50° C. (cf. the Preparation Examples).

The amino compounds of the formula (X) required as intermediates are known and/or can be prepared by processes known per se (cf. DE 3018134, DE 3804794, EP 298542, Preparation Examples).

A general definition of the (thio)carboxylic acid derivatives furthermore to be used as starting materials in the process (a) according to the invention for preparing the compounds of the formula (I) is given by the formula (III). In the formula (III), Q and $R^3$ each preferably or in particular have that meaning which has already been indicated above in connection with the description of the compounds of the formula (I) according to the invention as being preferred or, respectively, particularly preferred for Q and $R^3$; Z preferably represents fluorine, chlorine, bromine, $C_1$–$C_4$-alkoxy, phenoxy or benzyloxy, in particular chlorine, methoxy, ethoxy or phenoxy.

The starting materials of the formula (III) are known and/or can be prepared by processes known per se (cf. EP 459244, EP 341489, EP 422469, EP 425948, EP 431291, EP 507171, EP 534266).

A general definition of the sulphonyl iso(thio)cyanates to be used as starting materials in the process (b) according to the invention for preparing the compounds of the formula (I) is given by the formula (IV). In the formula (IV), A, Q, $R^1$ and $R^2$ each preferably or in particular have that meaning which has already been indicated above in connection with the description of the compounds of the formula (I) according to the invention as being preferred or, respectively, particularly preferred for A, Q, $R^1$ and $R^2$.

The starting materials of the formula (IV) are known and/or can be prepared by processes known per se (cf. EP 46626, U.S. Pat. No. 4,701,535, Preparation Examples).

A general definition of the heterocycles to be used as starting materials in the process (b), (c) and (e) according to the invention for preparing the compounds of the formula (I) is given by the formula (V). In the formula (V), $R^3$ preferably or in particular has that meaning which has already been indicated above in connection with the description of the compounds of the formula (I) according to the invention as being preferred or, respectively, particularly preferred for $R^3$.

The starting materials of the formula (V) are known and/or can be prepared by known processes (cf. EP 341489, EP 422469, EP 425948, EP 431291, EP 507171, EP 534266).

A general definition of the sulphonyl chlorides to be used as starting materials in the processes (c) and (d) according to the invention for preparing the compounds of the formula (I) is given by the formula (VI). In the formula (VI), A, $R^1$ and $R^2$ each preferably or in particular have that meaning which has already been indicated above in connection with the description of the compounds of the formula (I) according to the invention as being preferred or, respectively, particularly preferred for A, $R^1$ and $R^2$.

The starting materials of the formula (VI) are known and/or can be prepared by processes known per se (cf. U.S. Pat. Nos. 4,546,179, 5,084,086, 5,157,119, WO 8909214, WO 9115478, WO 9213845, Preparation Examples). However, as already mentioned, the compounds of the formula (VI) where A=S, i.e. the compunds of the sub-group of the formula (VIa), are novel.

A general definition of the (thio)carboxamides to be used as starting materials in the process (d) according to the invention for preparing the compounds of the formula (I) is given by the formula (VIII). In the formula (VIII), Q and $R^3$ each preferably or in particular have that meaning which has already been indicated above in connection with the description of the compounds of the formula (I) according to the invention as being preferred or, respectively, particularly preferred for Q and $R^3$.

The starting materials of the formula (VIII) are known and/or can be prepared by processes known per se (cf. EP 459244).

A general definition of the sulphonylamino(thio)carbonyl compounds to be used as starting materials in the process (e) according to the invention for preparing the compounds of the formula (I) is given by the formula (IX). In the formula (IX), A, Q, $R^1$ and $R^2$ each preferably or in particular have that meaning which has already been indicated above in connection with the description of the compounds of the formula (I) according to the invention as being preferred or, respectively, particularly preferred for A, Q, $R^1$ and $R^2$; Z preferably represents fluorine, chlorine, bromine, $C_1$–$C_4$-alkoxy, phenoxy or benzyloxy, in particular represents chlorine, methoxy, ethoxy or phenoxy.

The starting materials of the formula (IX) are known and/or can be prepared by methods known per se.

The processes (a), (b), (c), (d) and (e) according to the invention for the preparation of the novel compounds of the formula (I) are preferably carried out using diluents. Suitable diluents in this context are virtually all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene; ethers such as diethyl ether and dibutyl ether, glycol dimethyl ether and diglycol dimethyl ether, tetrahydrofuran and dioxane; ketones such as acetone, methyl ethyl ketone, methyl isopropyl ketone and methyl isobutyl ketone; esters such as methyl acetate and ethyl acetate; nitrites, for example acetonitrile and propionitrile; amides, for example dimethylformamide, dimethylacetamide and N-methylpyrrolidone, and also dimethyl sulphoxide, tetramethylene sulphone and hexamethylphosphorictriamide.

Suitable reaction auxiliaries and/or acid acceptors for the processes (a), (b), (c), (d) and (e) according to the invention are all acid-binding agents which are conventionally used for such reactions. Preference is given to alkali metal hydroxides, such as, for example, sodium hydroxide and potassium hydroxide, alkaline earth metal hydroxides such as, for example, calcium hydroxide, alkali metal carbonates and alkoxides, such as sodium carbonate and potassium carbonate, sodium tert-butoxide and potassium tert-butoxide, and also basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6dimethyl-, 2-ethyl-, 4-ethyl- and 5-ethyl-2-methyl-pyridine, 1,5-diazabicyclo[4,3,0]-non-5-ene (DBN), 1,8-diazabicyclo[5,4,0]-undec-7-ene (DBU) and 1,4-diazabicyclo-[2,2,2]-octane(DABCO).

The reaction temperatures in the processes (a), (b), (c), (d) and (e) according to the invention can be varied within a relatively wide range. The processes are in general carried out at temperatures of between −20° C. and +150° C., preferably at temperatures between 0° C. and +100° C.

The processes (a), (b), (c), (d) and (e) according to the invention are generally carried out under atmospheric pressure. However, it is also possible to operate under elevated or reduced pressure.

For carrying out processes (a), (b), (c), (d) and (e) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Work-up in the case of the processes (a), (b), (c), (d) and (e) according to the invention is in each case carried out by customary methods (cf. the Preparation Examples).

Salts can be prepared, if desired, from the compounds of the general formula (I) according to the invention. Such salts are obtained in a simple manner by customary methods of forming salts, for example by dissolving or dispersing a compound of the formula (I) in an appropriate solvent, for example methylene chloride, acetone, tert-butyl methyl ether or toluene, and adding an appropriate base. The salts can then—if desired after prolonged stirring—be isolated by concentration or filtration with suction.

The active compounds according to the invention can be used as defoliants, desiccants, haulm killers and, especially, as weed-killers. By weeds, in the broadest sense, are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous Weeds of the Genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous Cultures of the Genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous Weeds of the Genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous Cultures of the Genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, in lawns, turf and pasture-land, and for the selective control of weeds in annual crops.

The compounds of the formula (I) according to the invention are particularly suitable for the selective control of monocotyledonous and dicotyledonous weeds in monocotyledenous and dicotyledenous crops, both pre-emergence and post-emergence.

To some extent, the compounds of the formula (I) also have fungicidal activity, for example against Pyricularia oryzae on rice.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam formers.

If the extender used is water, it is also possible to use for example organic solvents as auxiliary solvents. Suitable liquid solvents essentially include: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoicesters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlorotoluron, diuron, fluometuron, isoproturon, linuron and methabenzthiazuron;hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulphonylureas, such as amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as, for example, butylate, cycloate, diallate, EPTC, esprocarb, molinate, prosulphocarb, thiobencarb and triallate; triazines, such as atrazine, cyanazine, simazine, simetryne, terbutryne and terbutylazine; triazinones, such as hexazinone, metamitron and metribuzin; and others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

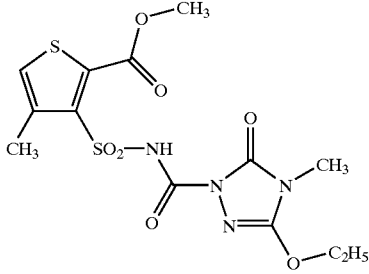

(Process (a))

7.5 g (32 mmol) of 4-methyl-2-methoxycarbonyl-thiophene-3-sulphonamide and 4.9 g (32 mmol) of 1,8-diazabicyclo-[5,4,0]-undec-7-ene (DBU) are added successively to a solution of 7.9 g (30 mmol) of 5-ethoxy-4-methyl-2-phenoxycarbonyl-2,4-dihydro-3H-1,2,4-triazol-3-one in 150 ml of acetonitrile. The reaction mixture is stirred at room temperature (about 20° C.) for about 15 hours and subsequently concentrated using water pump vacuum. The residue is then taken up in methylene chloride and washed with 1N hydrochloric acid and then with water. The organic phase is dried over magnesium sulphate and filtered. The filtrate is concentrated using water pump vacuum and the residue is recrystallized from isopropanol.

9.2 g (76% of theory) of 5-ethoxy-4-methyl-2-(4-methyl-2-methoxycarbonyl-thien-3-yl-sulphonylaminocarbonyl)-2,4-dihydro-3H-1,2,4-triazol-3-one of melting point 169° C. are obtained.

Example 2

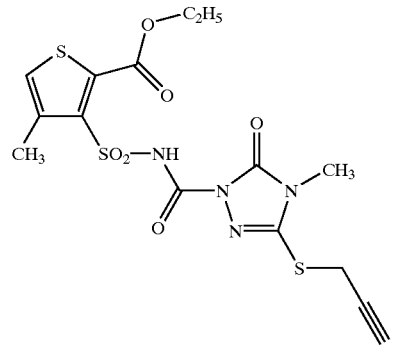

(Process (b))

2.1 g (8 mmol) of 2-ethoxycarbonyl-4-methyl-thien-3-yl-sulphonyl isocyanate are added to a solution of 1.35 g (8 mmol) of 4-methyl-5-propargylthio-2,4-dihydro-3H-1,2,4-triazol-3-one in 50 ml of acetonitrile. The mixture is then heated under reflux for 8 hours and subsequently concentrated using water pump vacuum, the residue is stirred with diethyl ether and the crystalline product is isolated by filtration with suction.

1.4 g (40% of theory) of 4-methyl-5-propargylthio-2-(2-ethoxycarbonyl-4-methyl-thien-3-yl-sulphonylaminocarbonyl)-2,4-dihydro-3H-1,2,4-triazol-3-one of melting point 175° C. are obtained.

Example 3

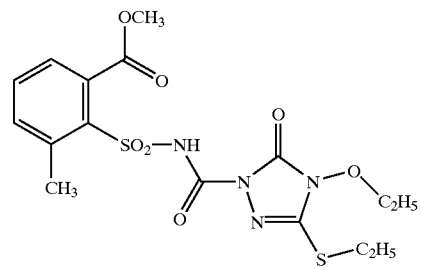

(Process (c))

A solution of 3.8 g (20 mmol) of 4-ethoxy-5-ethylthio-2,4-dihydro-3H-1,2,4-triazol-3-one in 50 ml of acetonitrile is admixed with 6.0 g (24 mmol) of 2-methyl-6-methoxy-carbonyl-benzenesulphonyl chloride, 2.6 g (40 mmol) of sodium cyanate and 1.2 g (15 mmol) of pyridine, and the reaction mixture is stirred at room temperature (about 20° C.) for 3 days. The mixture is then diluted with approximately identical volumina of methylene chloride and water to about three times its volume and then made weakly acidic (pH~3) using 1N hydrochloric acid. The organic phase is separated off, dried over sodium sulphate and filtered. The filtrate is concentrated and the residue is recrystallized from isopropanol.

5.0 g (56% of theory) of 4-ethoxy-5-ethylthio-2-(2-methyl-6-methoxy-carbonyl-phenylsulphonylaminocarbonyl)-2,4-dihydro-3H-1,2,4-triazol-3-one of melting point 135° C. are obtained.

Example 4

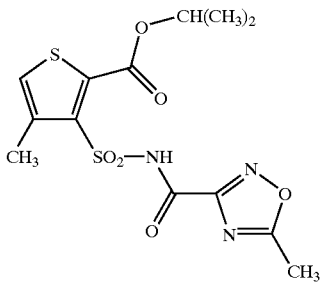

(Process (d))

At 20° C. to a maximum of 35° C., 2.0 g (36 mmol) of potassium hydroxide powder are added to a solution of 1.52 g (12.0 mmol) of 5-methyl-1,2,4-oxadiazole-3-carboxamide in 150 ml of dioxane. After 30 minutes, about 50 ml of dioxane are distilled off at 30° C. to 35° C. using water pump vacuum. The mixture is subsequently admixed a little at a time with 3.6 g (12.6 mmol) of 4-methyl-2-i-propoxycarbonyl-thiophene-3-sulphonyl chloride and the reaction mixture is stirred at room temperature (about 20° C.) for about 12 hours. The mixture is subsequently concentrated using water pump vacuum and the residue is taken up in water and acidified using 2N hydrochloric acid. The mixture is then extracted twice using 100 ml of methylene chloride each time. The combined organic solutions are washed with water, dried over magnesium sulphate and filtered. The filtrate is concentrated using water pump vacuum and the residue is recrystallized from ethanol.

2.3 g (52% of theory) of N-(4-methyl-2-i-propoxycarbonyl-thien-3-yl-sulphonyl)-5-methyl-1,2,4-oxadiazole-3-carboxamide of melting point 142° C. are obtained.

Similar to Examples 1 to 4, and according to the general description of the preparation processes according to the invention, it is also possible to prepare for example the compounds of the formula (I) listed in Table 1 below.

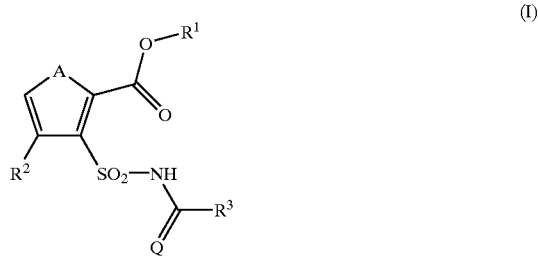

(I)

TABLE 1

Examples of compounds of the formula (I)

| Ex. No. | A | Q | $R^1$ | $R^2$ | $R^3$ | Melting point (° C.) |
|---|---|---|---|---|---|---|
| 5 | S | O | $CH_3$ | $CH_3$ | triazolinone with $CH_3$, $CH_3$, $C_2H_5$ | 178 |
| 6 | S | O | $CH_3$ | $CH_3$ | triazolinone with $CH_3$, $CH_3$, $S-CH_3$ | 192 |
| 7 | CH=CH | O | $C_2H_5$ | $CH_3$ | triazolinone with $CH_3$, $CH_3$, $S-CH_3$ | 154 |
| 8 | CH=CH | O | $C_3H_7$-i | $CH_3$ | triazolinone with $CH_3$, $CH_3$, $S-CH_3$ | 124 |

TABLE 1-continued
Examples of compounds of the formula (I)
| Ex. No. | A | Q | R¹ | R² | R³ | Melting point (° C.) |
|---|---|---|---|---|---|---|
| 9 | CH=CH | O | CH₃ | CH₃ | 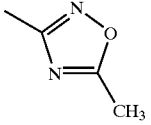 | 115 |
| 10 | CH=CH | O | C₂H₅ | CH₃ | 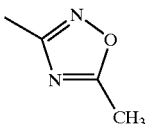 | 85 |
| 11 | CH=CH | O | C₃H₇-n | CH₃ | 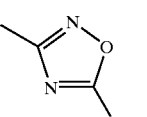 | 59 |
| 12 | CH=CH | O | C₃H₇-i | CH₃ | 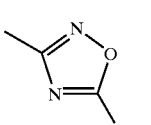 | (amorphous) |
| 13 | S | O | CH₃ | CH₃ | 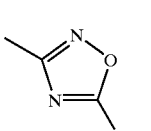 | 157 |
| 14 | S | O | CH₃ | CH₃ | 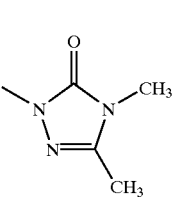 | 158 |
| 15 | CH=CH | O | C₂H₅ | CH₃ | 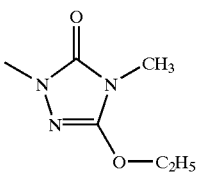 | 168 |
| 16 | CH=CH | O | C₃H₇-i | CH₃ | 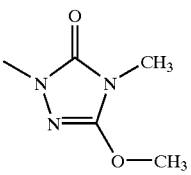 | 144 |
| 17 | CH=CH | O | C₃H₇-i | CH₃ | 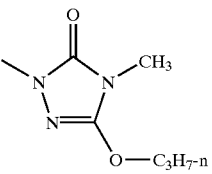 | 122 |

TABLE 1-continued

Examples of compounds of the formula (I)

| Ex. No. | A | Q | R¹ | R² | R³ | Melting point (° C.) |
|---|---|---|---|---|---|---|
| 18 | CH=CH | O | C₃H₇-i | CH₃ | 1-methyl-4-methyl-5-(i-propoxy)-1,2,4-triazol-3(2H)-one | 167 |
| 19 | CH=CH | O | C₃H₇-i | CH₃ | 1-methyl-4-ethyl-5-methoxy-1,2,4-triazol-3(2H)-one | 114 |
| 20 | CH=CH | O | C₃H₇-n | CH₃ | 1-methyl-4-methyl-5-methoxy-1,2,4-triazol-3(2H)-one | 142 |
| 21 | CH=CH | O | C₃H₇-n | CH₃ | 1-methyl-4-methyl-5-ethoxy-1,2,4-triazol-3(2H)-one | 106 |
| 22 | CH=CH | O | C₃H₇-n | CH₃ | 1-methyl-4-methyl-5-(n-propoxy)-1,2,4-triazol-3(2H)-one | 105 |
| 23 | CH=CH | O | C₃H₇-n | CH₃ | 1-methyl-4-methyl-5-(i-propoxy)-1,2,4-triazol-3(2H)-one | 112 |
| 24 | CH=CH | O | C₃H₇-n | CH₃ | 1-methyl-4-ethyl-5-methoxy-1,2,4-triazol-3(2H)-one | 115 |
| 25 | CH=CH | O | C₃H₇-n | CH₃ | 1-methyl-4-ethoxy-5-ethyl-1,2,4-triazol-3(2H)-one | 77 |

TABLE 1-continued

Examples of compounds of the formula (I)

| Ex. No. | A | Q | R¹ | R² | R³ | Melting point (° C.) |
|---|---|---|---|---|---|---|
| 26 | CH=CH | O | C₃H₇-i | CH₃ | 1-methyl-4-ethoxy-5-ethyl-1,2,4-triazol-3(4H)-one | 131 |
| 27 | S | O | CH₃ | CH₃ | 1,4-dimethyl-5-bromo-1,2,4-triazol-3(4H)-one | 158 |
| 28 | S | O | CH₃ | CH₃ | 1-methyl-4-cyclopropyl-5-methoxymethyl-1,2,4-triazol-3(4H)-one | 175 |
| 29 | S | O | CH₃ | CH₃ | 1-methyl-4-cyclopropyl-5-bromo-1,2,4-triazol-3(4H)-one | 151 |
| 30 | S | O | CH₃ | CH₃ | 1-methyl-4-cyclopropyl-5-ethoxy-1,2,4-triazol-3(4H)-one | 155 |
| 31 | S | O | CH₃ | CH₃ | 1,4-dimethyl-5-methoxy-1,2,4-triazol-3(4H)-one | 184 |
| 32 | S | O | CH₃ | CH₃ | 1,4-dimethyl-5-methoxymethyl-1,2,4-triazol-3(4H)-one | 151 |
| 33 | S | O | CH₃ | CH₃ | 1,4-dimethyl-5-n-propoxy-1,2,4-triazol-3(4H)-one | 191 |

TABLE 1-continued

Examples of compounds of the formula (I)

| Ex. No. | A | Q | R¹ | R² | R³ | Melting point (° C.) |
|---|---|---|---|---|---|---|
| 34 | S | O | CH₃ | CH₃ | 1,4-dimethyl-5-(ethylthio)-1,2,4-triazol-3(4H)-one | 142 |
| 35 | S | O | CH₃ | CH₃ | 1,4-dimethyl-5-(n-propyl)-1,2,4-triazol-3(4H)-one | 122 |
| 36 | S | O | CH₃ | CH₃ | 1,4-dimethyl-5-(i-propyl)-1,2,4-triazol-3(4H)-one | 121 |
| 37 | S | O | CH₃ | CH₃ | 4-ethyl-5-methoxy-1-methyl-1,2,4-triazol-3(4H)-one | 187 |
| 38 | S | O | CH₃ | CH₃ | 4-ethoxy-5-ethyl-1-methyl-1,2,4-triazol-3(4H)-one | 163 |
| 39 | S | O | CH₃ | CH₃ | 4-methoxy-1-methyl-5-(n-propyl)-1,2,4-triazol-3(4H)-one | 124 |
| 40 | S | O | CH₃ | CH₃ | 1,4-dimethyl-5-(i-propoxy)-1,2,4-triazol-3(4H)-one | 162 |
| 41 | S | O | CH₃ | CH₃ | 5-ethoxy-4-ethyl-1-methyl-1,2,4-triazol-3(4H)-one | 144 |

TABLE 1-continued

Examples of compounds of the formula (I)

| Ex. No. | A | Q | R¹ | R² | R³ | Melting point (° C.) |
|---|---|---|---|---|---|---|
| 42 | CH=CH | O | $C_3H_7$-i | $CH_3$ | 1-methyl-4-methyl-5-(ethylthio)-1,2,4-triazol-3(4H)-one | 125 |
| 43 | CH=CH | O | $C_3H_7$-i | $CH_3$ | 1-methyl-4-ethyl-5-ethoxy-1,2,4-triazol-3(4H)-one | 120 |
| 44 | CH=CH | O | $C_3H_7$-i | $CH_3$ | 1-methyl-4-methyl-5-ethoxy-1,2,4-triazol-3(4H)-one | 121 |
| 45 | CH=CH | O | $C_3H_7$-n | $CH_3$ | 1-methyl-4-ethyl-5-ethoxy-1,2,4-triazol-3(4H)-one | 118 |
| 46 | CH=CH | O | $C_3H_7$-i | $CH_3$ | 1-methyl-4-cyclopropyl-5-ethoxy-1,2,4-triazol-3(4H)-one | 130 |
| 47 | CH=CH | O | $C_3H_7$-n | $CH_3$ | 1-methyl-4-methyl-5-(n-propyl)-1,2,4-triazol-3(4H)-one | 107 |
| 48 | CH=CH | O | $C_3H_7$-n | $CH_3$ | 1-methyl-4-methyl-5-(ethylthio)-1,2,4-triazol-3(4H)-one | 87 |
| 49 | CH=CH | O | $CH_2CF_3$ | $CH_3$ | 3-methyl-5-methyl-1,2,4-oxadiazole | 113 |

TABLE 1-continued

Examples of compounds of the formula (I)

| Ex. No. | A | Q | R¹ | R² | R³ | Melting point (° C.) |
|---|---|---|---|---|---|---|
| 50 | CH=CH | O | C₃H₇-n | CH₃ | triazolinone with N-CH₃, N-CH₃, O-CH₂-CF₃ | 122 |
| 51 | S | | O | CH₃ | CH₃ | triazolinone with N-CH₃, N-CH₃, S-CH₂-C≡CH | 137 |
| 52 | S | | O | CH₃ | CH₃ | triazolinone with N-CH₃, N-CH₃, O-CH₂-CF₃ | 185 |
| 53 | S | | O | CH₃ | CH₃ | triazolinone with N-CH₃, N-cyclopropyl, O-C₃H₇-i | 184 |
| 54 | S | | O | C₂H₅ | CH₃ | triazolinone with N-CH₃, N-CH₃, O-C₂H₅ | 161 |
| 55 | S | | O | C₂H₅ | CH₃ | triazolinone with N-CH₃, N-CH₃, S-CH₃ | 131 |

TABLE 1-continued

Examples of compounds of the formula (I)

| Ex. No. | A | Q | R¹ | R² | R³ | Melting point (° C.) |
|---|---|---|---|---|---|---|
| 56 | S | O | $C_2H_5$ | $CH_3$ | 1,4-dimethyl-5-(ethylthio)-1,2,4-triazol-3(4H)-one-yl | 158 |
| 57 | S | O | $C_2H_5$ | $CH_3$ | 1,4-dimethyl-5-methoxy-1,2,4-triazol-3(4H)-one-yl | 178 |
| 58 | S | O | $C_2H_5$ | $CH_3$ | 1,4-dimethyl-5-(n-propoxy)-1,2,4-triazol-3(4H)-one-yl | 133 |
| 59 | S | O | $C_2H_5$ | $CH_3$ | 1,4-dimethyl-5-(i-propoxy)-1,2,4-triazol-3(4H)-one-yl | 131 |
| 60 | S | O | $C_2H_5$ | $CH_3$ | 1-methyl-4-ethyl-5-methoxy-1,2,4-triazol-3(4H)-one-yl | 159 |
| 61 | S | O | $C_2H_5$ | $CH_3$ | 1-methyl-4-ethoxy-5-ethyl-1,2,4-triazol-3(4H)-one-yl | 132 |
| 62 | S | O | $C_2H_5$ | $CH_3$ | 1,4-dimethyl-5-(2,2,2-trifluoroethoxy)-1,2,4-triazol-3(4H)-one-yl | 150 |

TABLE 1-continued

Examples of compounds of the formula (I)

| Ex. No. | A | Q | R¹ | R² | R³ | Melting point (° C.) |
|---|---|---|---|---|---|---|
| 63 | S | O | $C_2H_5$ | $CH_3$ | 1-methyl-4-cyclopropyl-5-ethoxy-1,2,4-triazol-3(4H)-one | 142 |
| 64 | S | O | $C_2H_5$ | $CH_3$ | 1-methyl-4-ethyl-5-ethoxy-1,2,4-triazol-3(4H)-one | 108 |
| 65 | S | O | $C_2H_5$ | $CH_3$ | 1,4-dimethyl-5-methyl-1,2,4-triazol-3(4H)-one | 123 |
| 66 | S | O | $C_2H_5$ | $CH_3$ | 1,4-dimethyl-5-ethyl-1,2,4-triazol-3(4H)-one | 135 |
| 67 | S | O | $C_2H_5$ | $CH_3$ | 1,4-dimethyl-5-n-propyl-1,2,4-triazol-3(4H)-one | 77 |
| 68 | S | O | $C_2H_5$ | $CH_3$ | 1,4-dimethyl-5-isopropyl-1,2,4-triazol-3(4H)-one | 130 |
| 69 | S | O | $C_2H_5$ | $CH_3$ | 1-methyl-4-methoxy-5-n-propyl-1,2,4-triazol-3(4H)-one | 141 |
| 70 | S | O | $C_2H_5$ | $CH_3$ | 1-methyl-4-cyclopropyl-5-isopropoxy-1,2,4-triazol-3(4H)-one | 141 |

TABLE 1-continued

Examples of compounds of the formula (I)

| Ex. No. | A | Q | R¹ | R² | R³ | Melting point (° C.) |
|---|---|---|---|---|---|---|
| 71 | CH=H | O | $C_3H_7$-i | $CF_3$ | 3-methyl-5-methyl-1,2,4-oxadiazol-yl | 73 |
| 72 | S | O | $C_2H_5$ | $CH_3$ | 3-methyl-5-methyl-1,2,4-oxadiazol-yl | 139 |
| 73 | CH=CH | O | $CH_3$ | $OCF_3$ | 2-methyl-4-ethyl-5-ethoxy-1,2,4-triazol-3-one-yl | 181 |
| 74 | CH=CH | O | $CH_3$ | $OCF_3$ | 3-methyl-5-methyl-1,2,4-oxadiazol-yl | 107 |
| 75 | S | O | $C_3H_7$-n | $CH_3$ | 3-methyl-5-methyl-1,2,4-oxadiazol-yl | 114 |
| 76 | S | O | $C_3H_7$-i | $CH_3$ | 2-methyl-4-methyl-5-ethoxy-1,2,4-triazol-3-one-yl | 152 |
| 77 | S | O | $C_3H_7$-i | $CH_3$ | 2-methyl-4-methyl-5-ethyl-1,2,4-triazol-3-one-yl | 146 |
| 78 | S | O | $C_3H_7$-i | $CH_3$ | 2-methyl-4-methyl-5-methylthio-1,2,4-triazol-3-one-yl | 164 |
| 79 | S | O | $C_3H_7$-n | $CH_3$ | 2-methyl-4-methyl-5-methylthio-1,2,4-triazol-3-one-yl | 167 |

TABLE 1-continued

Examples of compounds of the formula (I)

| Ex. No. | A | Q | R¹ | R² | R³ | Melting point (° C.) |
|---|---|---|---|---|---|---|
| 80 | S | O | $C_3H_7$-n | $CH_3$ | 1,4-dimethyl-3-oxo-1,2,4-triazol-5-yl O-$C_2H_5$ | 113 |
| 81 | S | O | $C_3H_7$-i | $CH_3$ | 1,4-dimethyl-3-oxo-1,2,4-triazol-5-yl S-$C_2H_5$ | 131 |
| 82 | S | O | $C_3H_7$-i | $CH_3$ | 1,4-dimethyl-3-oxo-1,2,4-triazol-5-yl O-$CH_3$ | 173 |
| 83 | S | O | $C_3H_7$-i | $CH_3$ | 1,4-dimethyl-3-oxo-1,2,4-triazol-5-yl O-$C_3H_7$-n | 87 |
| 84 | S | O | $C_3H_7$i | $CH_3$ | 1,4-dimethyl-3-oxo-1,2,4-triazol-5-yl O-$C_3H_7$-i | 125 |
| 85 | S | O | $C_3H_7$-i | $CH_3$ | 1-methyl-4-cyclopropyl-3-oxo-1,2,4-triazol-5-yl O-$C_2H_5$ | 127 |
| 86 | S | O | $C_3H_7$-i | $CH_3$ | 1-methyl-4-ethyl-3-oxo-1,2,4-triazol-5-yl O-$C_2H_5$ | 126 |
| 87 | S | O | $C_3H_7$-i | $CH_3$ | 1-methyl-4-cyclopropyl-3-oxo-1,2,4-triazol-5-yl O-$C_3H_7$-i | 136 |

TABLE 1-continued
Examples of compounds of the formula (I)
| Ex. No. | A | Q | R¹ | R² | R³ | Melting point (° C.) |
|---|---|---|---|---|---|---|
| 88 | S | O | $C_2H_5$ | $CH_3$ | 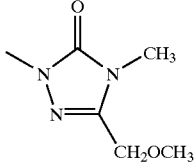 | 106 |
| 89 | S | O | $C_3H_7$-n | $CH_3$ | 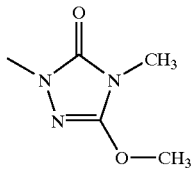 | 117 |
| 90 | S | O | $C_3H_7$-n | $CH_3$ | 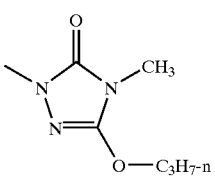 | 90 |
| 91 | S | O | $C_3H_7$-n | $CH_3$ | 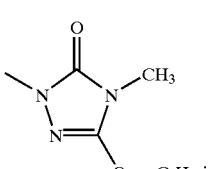 | 134 |
| 92 | S | O | $C_3H_7$-n | $CH_3$ | 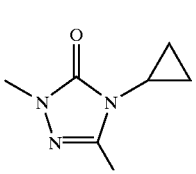 | 141 |
| 93 | S | O | $C_3H_7$-n | $CH_3$ | 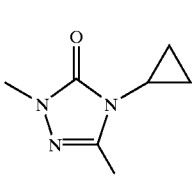 | 142 |
| 94 | S | O | $C_3H_7$-n | $CH_3$ | 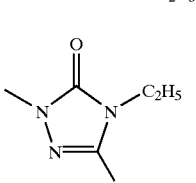 | 90 |
| 95 | S | O | $C_3H_7$-n | $CH_3$ | 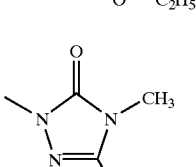 | 119 |

TABLE 1-continued

Examples of compounds of the formula (I)

| Ex. No. | A | Q | R¹ | R² | R³ | Melting point (° C.) |
|---|---|---|---|---|---|---|
| 96 | S | O | $C_3H_7$-i | $CH_3$ | 1-methyl-4-cyclopropyl-5-bromo-1,2,4-triazol-3(4H)-one | 159 |
| 97 | S | O | $C_3H_7$-i | $CH_3$ | 1-methyl-4-cyclopropyl-5-($CH_2OCH_3$)-1,2,4-triazol-3(4H)-one | 130 |
| 98 | S | O | $C_3H_7$-i | $CH_3$ | 1-methyl-4-($OC_2H_5$)-5-$C_2H_5$-1,2,4-triazol-3(4H)-one | 145 |
| 99 | S | O | $C_3H_7$-n | $CH_3$ | 1-methyl-4-$CH_3$-5-$CH_3$-1,2,4-triazol-3(4H)-one | 109 |
| 100 | S | O | $C_3H_7$-n | $CH_3$ | 1-methyl-4-$CH_3$-5-($C_3H_7$-n)-1,2,4-triazol-3(4H)-one | 95 |
| 101 | S | O | $C_3H_7$-n | $CH_3$ | 1-methyl-4-$CH_3$-5-($C_3H_7$-i)-1,2,4-triazol-3(4H)-one | 84 |
| 102 | S | O | $C_3H_7$-n | $CH_3$ | 1-methyl-4-cyclopropyl-5-($CH_2OCH_3$)-1,2,4-triazol-3(4H)-one | 89 |
| 103 | S | O | $C_3H_7$-n | $CH_3$ | 1-methyl-4-cyclopropyl-5-(O—$C_3H_7$-i)-1,2,4-triazol-3(4H)-one | 135 |

TABLE 1-continued

Examples of compounds of the formula (I)

| Ex. No. | A | Q | R¹ | R² | R³ | Melting point (° C.) |
|---|---|---|---|---|---|---|
| 104 | S | O | $C_2H_5$ | $CH_3$ | 3-methyl-4-cyclopropyl-5-(methoxymethyl)-1,2,4-triazol-5(4H)-one | 155 |
| 105 | S | O | $C_2H_5$ | $CH_3$ | 2-methyl-4-methyl-5-bromo-1,2,4-triazol-3(2H)-one | 116 |
| 106 | S | O | $C_2H_5$ | $CH_3$ | 2-methyl-4-cyclopropyl-5-bromo-1,2,4-triazol-3(2H)-one | 136 |
| 107 | S | O | $C_3H_7$-i | $CH_3$ | 2-methyl-4-methyl-5-methyl-1,2,4-triazol-3(2H)-one | 135 |
| 108 | S | O | $C_3H_7$-i | $CH_3$ | 2-methyl-4-methyl-5-(n-propyl)-1,2,4-triazol-3(2H)-one | 98 |
| 109 | S | O | $C_3H_7$-i | $CH_3$ | 2-methyl-4-methyl-5-(i-propyl)-1,2,4-triazol-3(2H)-one | 120 |
| 110 | S | O | $C_3H_7$-i | $CH_3$ | 2-methyl-4-ethyl-5-methoxy-1,2,4-triazol-3(2H)-one | 140 |
| 111 | S | O | $C_3H_7$-i | $CH_3$ | 2-methyl-4-methyl-5-bromo-1,2,4-triazol-3(2H)-one | 137 |

TABLE 1-continued

Examples of compounds of the formula (I)

| Ex. No. | A | Q | R¹ | R² | R³ | Melting point (° C.) |
|---|---|---|---|---|---|---|
| 112 | S | O | $C_3H_7$-i | $CH_3$ | 1-methyl-4-methyl-5-(OCH₂CF₃)-1,2,4-triazol-3(4H)-one | 145 |
| 113 | S | O | $C_3H_7$-i | $CH_3$ | 1-methyl-4-methoxy-5-(n-C₃H₇)-1,2,4-triazol-3(4H)-one | 124 |
| 114 | S | O | $C_3H_7$-n | $CH_3$ | 1-methyl-4-ethyl-5-(OCH₃)-1,2,4-triazol-3(4H)-one | 108 |
| 115 | S | O | $C_3H_7$-n | $CH_3$ | 1-methyl-4-(OC₂H₅)-5-(C₂H₅)-1,2,4-triazol-3(4H)-one | 138 |
| 116 | S | O | $C_3H_7$-n | $CH_3$ | 1-methyl-4-methyl-5-Br-1,2,4-triazol-3(4H)-one | 93 |
| 117 | S | O | $C_3H_7$-n | $CH_3$ | 1-methyl-4-methyl-5-(OCH₂CF₃)-1,2,4-triazol-3(4H)-one | 130 |
| 118 | S | O | $C_3H_7$-n | $CH_3$ | 1-methyl-4-methoxy-5-(n-C₃H₇)-1,2,4-triazol-3(4H)-one | 128 |

TABLE 1-continued
Examples of compounds of the formula (I)
| Ex. No. | A | Q | R¹ | R² | R³ | Melting point (° C.) |
|---|---|---|---|---|---|---|
| 119 | S | O | CH₃ | CH₃ | 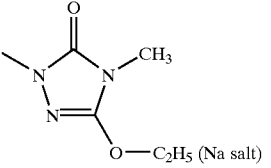 | 248 |
| 120 | CH=CH | O | CH₃ | Cl | 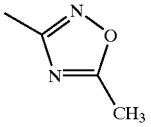 | 78 |
| 121 | CH=CH | O | CH₃ | CH₃ | 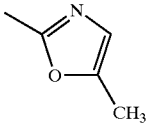 | 120 |
| 122 | CH=CH | O | CH₃ | Cl | 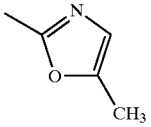 | 68 |
| 123 | CH=CH | O | CH₃ | CH₃ | 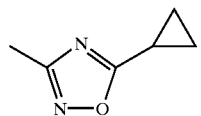 | 54 |
| 124 | CH=CH | O | CH₃ | Cl | 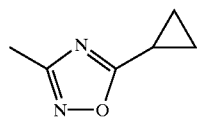 | 147 |
| 125 | CH=CH | O | CH₃ | CH₃ | 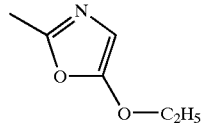 | 118 |
| 126 | CH=CH | O | CH₃ | Cl | 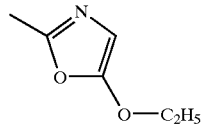 | 63 |
| 127 | CH=CH | O | CH₃ | Cl | 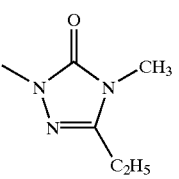 | 167 |

TABLE 1-continued

Examples of compounds of the formula (I)

| Ex. No. | A | Q | R¹ | R² | R³ | Melting point (° C.) |
|---|---|---|---|---|---|---|
| 128 | CH=CH | O | $C_2H_5$ | Cl | ![structure: 1,4-dimethyl-5-ethyl-1,2,4-triazol-3(4H)-one] | 128 |
| 129 | CH=CH | O | $CH_3$ | Cl | ![structure: 1,4-dimethyl-5-ethoxy-1,2,4-triazol-3(4H)-one] | 95 |
| 130 | CH=CH | O | $CH_3$ | Cl | ![structure: 1,4-dimethyl-5-methylthio-1,2,4-triazol-3(4H)-one] | 153 |
| 131 | CH=CH | O | $C_2H_5$ | Cl | ![structure: 1,4-dimethyl-5-methylthio-1,2,4-triazol-3(4H)-one] | 145 |
| 132 | CH=CH | O | $C_3H_7$-n | Cl | ![structure: 1,4-dimethyl-5-methylthio-1,2,4-triazol-3(4H)-one] | 98 |
| 133 | CH=CH | O | $C_3H_7$-n | Cl | ![structure: 1,4-dimethyl-5-ethyl-1,2,4-triazol-3(4H)-one] | 89 |
| 134 | CH=CH | O | $C_3H_7$-n | Cl | ![structure: 1,4-dimethyl-5-ethoxy-1,2,4-triazol-3(4H)-one] | 110 |
| 135 | CH=CH | O | $CH_3$ | $OCH_3$ | ![structure: 1-methyl-4-cyclopropyl-5-isopropoxy-1,2,4-triazol-3(4H)-one] | 175 |

TABLE 1-continued

Examples of compounds of the formula (I)

| Ex. No. | A | Q | R$^1$ | R$^2$ | R$^3$ | Melting point (° C.) |
|---|---|---|---|---|---|---|
| 136 | CH=CH | O | CH$_3$ | OCH$_3$ | 2,4-dimethyl-5-ethoxy-1,2,4-triazol-3(4H)-on-yl | 190 |
| 137 | CH=CH | O | C$_3$H$_7$-i | Cl | 2,4-dimethyl-5-ethoxy-1,2,4-triazol-3(4H)-on-yl | 89 |
| 138 | CH=CH | O | oxetan-3-yl | CH$_3$ | 2,4-dimethyl-5-ethoxy-1,2,4-triazol-3(4H)-on-yl | 146 |
| 139 | CH=CH | O | oxetan-3-yl | CH$_3$ | 2,4-dimethyl-5-methylthio-1,2,4-triazol-3(4H)-on-yl | 158 |
| 140 | CH=CH | O | CH$_3$ | CH$_3$ | 2,4-dimethyl-5-(n-propoxy)-1,2,4-triazol-3(4H)-on-yl | 150 |
| 141 | CH=CH | O | CH$_3$ | CH$_3$ | 2,4-dimethyl-5-ethylthio-1,2,4-triazol-3(4H)-on-yl | 142 |
| 142 | CH=CH | O | CH$_3$ | CH$_3$ | 2-methyl-4-cyclopropyl-5-(2,2,2-trifluoroethoxy)-1,2,4-triazol-3(4H)-on-yl | 145 |

TABLE 1-continued

Examples of compounds of the formula (I)

| Ex. No. | A | Q | R¹ | R² | R³ | Melting point (° C.) |
|---|---|---|---|---|---|---|
| 143 | CH=CH | O | CH₃ | CH₃ | ![structure: 1,4-dimethyl-triazolone with O-CH₂-CF₃] | 148 |
| 144 | CH=CH | O | CH₃ | CH₃ | ![structure: 1,4-dimethyl-triazolone with O-C₃H₇-n (Na salt)] | 155 |
| 145 | CH=CH | O | CH₃ | CH₃ | ![structure: 1,4-dimethyl-triazolone with S-CH₃ (Na salt)] | 185 |
| 146 | CH=CH | O | CH₃ | CH₃ | ![structure: N-methyl, N-OC₂H₅ triazolone with S-CH₃] | 163 |
| 147 | CH=CH | O | CH₃ | CH₃ | ![structure: N-methyl, N-cyclopropyl triazolone with O-allyl] | 122 |
| 148 | CH=CH | O | CH₃ | CH₃ | ![structure: 1,4-dimethyl-triazolone with O-allyl] | 137 |

TABLE 1-continued

Examples of compounds of the formula (I)

| Ex. No. | A | Q | R¹ | R² | R³ | Melting point (° C.) |
|---|---|---|---|---|---|---|
| 149 | CH=CH | O | $CH_3$ | $CH_3$ | 4-cyclopropyl-2-methyl-5-(2,2,2-trifluoroethylthio)-2,4-dihydro-3H-1,2,4-triazol-3-one | 156 |
| 150 | CH=CH | O | $CH_3$ | $CH_3$ | 2,4-dimethyl-5-(2,2,2-trifluoroethylthio)-2,4-dihydro-3H-1,2,4-triazol-3-one | 122 |
| 151 | CH=CH | O | $CH_3$ | $CH_3$ | 4-cyclopropyl-5-(2-fluoroethylthio)-2-methyl-2,4-dihydro-3H-1,2,4-triazol-3-one | 166 |
| 152 | CH=CH | O | $CH_3$ | $CH_3$ | 5-(2-fluoroethylthio)-2,4-dimethyl-2,4-dihydro-3H-1,2,4-triazol-3-one | 125 |
| 153 | CH=CH | O | $CH_3$ | $CH_3$ | 4-allyl-5-(2-fluoroethylthio)-2-methyl-2,4-dihydro-3H-1,2,4-triazol-3-one | 137 |
| 154 | CH=CH | O | $CH_3$ | $CH_3$ | 2,4-dimethyl-5-(n-propyl)-2,4-dihydro-3H-1,2,4-triazol-3-one, $C_3H_7$-n (Na salt) | 179 |
| 155 | CH=CH | O | $CH_3$ | $CH_3$ | 5-ethyl-4-ethoxy-2-methyl-2,4-dihydro-3H-1,2,4-triazol-3-one, $C_2H_5$ | 153 |

TABLE 1-continued

Examples of compounds of the formula (I)

| Ex. No. | A | Q | R¹ | R² | R³ | Melting point (° C.) |
|---|---|---|---|---|---|---|
| 156 | CH=CH | O | $CH_3$ | $CH_3$ | 1-methyl-4-methoxy-5-(methylthio)-1,2,4-triazol-3(4H)-one | 172 |
| 157 | CH=CH | O | $CH_3$ | $CH_3$ | 1-methyl-4-methoxy-5-(ethylthio)-1,2,4-triazol-3(4H)-one | 124 |
| 158 | CH=CH | O | $CH_3$ | $CH_3$ | 1-methyl-4-cyclopropyl-5-(methylthio)-1,2,4-triazol-3(4H)-one | 157 |
| 159 | CH=CH | O | $CH_3$ | $CH_3$ | 1-methyl-4-cyclopropyl-5-(ethylthio)-1,2,4-triazol-3(4H)-one | 156 |
| 160 | CH=CH | O | $CH_3$ | $CH_3$ | 1-methyl-4-cyclopropyl-5-(prop-2-ynylthio)-1,2,4-triazol-3(4H)-one | 138 |
| 161 | CH=CH | O | $CH_3$ | $CH_3$ | 1,4-dimethyl-5-(prop-2-ynylthio)-1,2,4-triazol-3(4H)-one | 137 |
| 162 | CH=CH | O | $CH_3$ | $CH_3$ | 1,4-dimethyl-5-methoxy-1,2,4-triazol-3(4H)-one | 160 |

TABLE 1-continued

Examples of compounds of the formula (I)

| Ex. No. | A | Q | R¹ | R² | R³ | Melting point (° C.) |
|---|---|---|---|---|---|---|
| 163 | CH=CH | O | CH₃ | CH₃ | 1,4-dimethyl-5-ethoxy-1,2,4-triazol-3(4H)-one-yl | 139 |
| 164 | CH=CH | O | CH₃ | CH₃ | 1-methyl-4-cyclopropyl-5-methoxy-1,2,4-triazol-3(4H)-one-yl | 174 |
| 165 | CH=CH | O | CH₃ | CH₃ | 1-methyl-4-cyclopropyl-5-n-propoxy-1,2,4-triazol-3(4H)-one-yl | 119 |
| 166 | CH=CH | O | CH₃ | CH₃ | 1-methyl-4-cyclopropyl-5-i-propoxy-1,2,4-triazol-3(4H)-one-yl | 158 |
| 167 | CH=CH | O | CH₃ | CH₃ | 1,4-dimethyl-5-cyclopropylmethoxy-1,2,4-triazol-3(4H)-one-yl | 148 |
| 168 | CH=CH | O | CH₃ | CH₃ | 1,4-dimethyl-5-sec-butoxy-1,2,4-triazol-3(4H)-one-yl | 128 |
| 169 | CH=CH | O | CH₃ | CH₃ | 1,4-dimethyl-5-phenoxy-1,2,4-triazol-3(4H)-one-yl | 145 |

TABLE 1-continued
Examples of compounds of the formula (I)
| Ex. No. | A | Q | R¹ | R² | R³ | Melting point (° C.) |
|---|---|---|---|---|---|---|
| 170 | CH=CH | O | CH₃ | CH₃ | 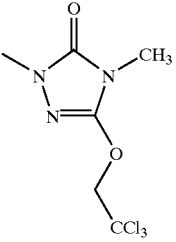 | 161 |
| 171 | CH=CH | O | CH₃ | CH₃ | 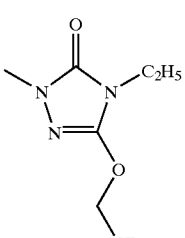 | 129 |
| 172 | CH=CH | O | CH₃ | CH₃ | 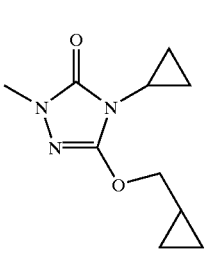 | 136 |
| 173 | CH=CH | O | CH₃ | CH₃ | 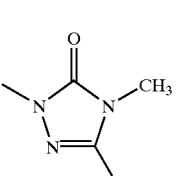 | 155 |
| 174 | CH=CH | O | CH₃ | CH₃ | 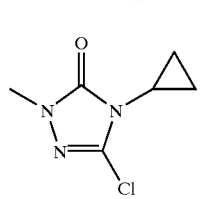 | 129 |
| 175 | CH=CH | O | CH₃ | CH₃ | 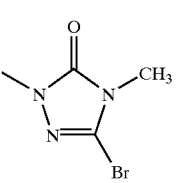 | 150 |
| 176 | CH=CH | O | CH₃ | CH₃ | 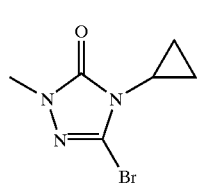 | 148 |

TABLE 1-continued

Examples of compounds of the formula (I)

| Ex. No. | A | Q | R¹ | R² | R³ | Melting point (° C.) |
|---|---|---|---|---|---|---|
| 177 | CH=CH | O | CH₃ | CH₃ | ![structure: 2,4-dimethyl-3-oxo-1,2,4-triazol-5-yl-O-CH₂-CF₂-CHF₂] | 149 |
| 178 | CH=CH | O | CH₃ | CH₃ | ![structure: 2-methyl-4-methoxy-3-oxo-1,2,4-triazol-5-yl-S-C₃H₇-n] | 99 |
| 179 | CH=CH | O | CH₃ | CH₃ | ![structure: 2-methyl-4-methoxy-3-oxo-1,2,4-triazol-5-yl-S-C₃H₇-i] | 115 |
| 180 | CH=CH | O | CH₃ | CH₃ | ![structure: 2-methyl-4-methoxy-3-oxo-1,2,4-triazol-5-yl-S-allyl] | 114 |
| 181 | CH=CH | O | CH₃ | CH₃ | ![structure: 2-methyl-4-methoxy-3-oxo-1,2,4-triazol-5-yl-S-propargyl] | 125 |
| 182 | CH=cH | O | CH₃ | CH₃ | ![structure: 2-methyl-4-methoxy-3-oxo-1,2,4-triazol-5-yl-S-CH₂CH₂F] | 124 |

TABLE 1-continued

Examples of compounds of the formula (I)

| Ex. No. | A | Q | R¹ | R² | R³ | Melting point (° C.) |
|---|---|---|---|---|---|---|
| 183 | CH=CH | O | CH₃ | CH₃ | | 105 |
| 184 | CH=CH | O | CH₃ | CH₃ | | 131 |
| 185 | CH=CH | O | CH₃ | CH₃ | | 149 |
| 186 | S | O | C₃H₇-n | CH₃ | | |
| 187 | CH=CH | O | CH₃ | NO₂ | | 180 |

The compound listed as Example 119 in Table 1 can be prepared for example as follows:

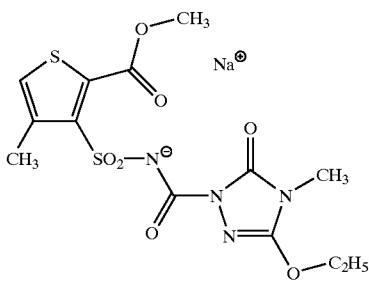

(Salt Formation)

A mixture of 2.0 g (5 mmol) of 5-ethoxy-4-methyl-2-(4methyl-2-methoxy-carbonyl-thien-3-yl-sulfonylaminocarbonyl)-2,4-dihydro-3H-1,2,4-triazol-3-one and 75 ml of acetonitrile is admixed with 0.17 g (5.5 mmol) of sodium hydride (80% strength), and the mixture is stirred at room temperature (about 20° C.) for about 60 minutes. The crystalline product is then isolated by filtration with suction 2.0 g (94% of theory) of the sodium salt of 5-ethoxy-4-methyl-2-(4-methyl-2-methoxycarbonyl-thien-3-yl-sulfonylaminocarbonyl)-2,4-dihydro-3H-1,2,4-triazol-3-one are obtained as a colourless crystalline product of melting point 248° C.

Starting Materials of the Formula (II)

Example (II-1)

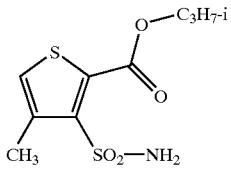

12.0 g (42.6 mmol) of 4-methyl-2-i-propoxycarbonyl-thiophene-3-sulfonyl chloride are dissolved in 100 ml of methylene chloride and admixed with 8.2 g (85.4 mmol) of ammonium carbonate. The mixture is stirred at room temperature (about 20° C.) for about 24 hours. The undissolved salt is filtered off by suction, the filtrate is concentrated using water pump vacuum, the residue is digested with diethyl ether and the crystalline product is isolated by filtration with suction.

9.1 g (91% of theory) of 4-methyl-2-i-propoxycarbonyl-thiophene-3-sulphonamide are obtained as a light-yellow solid of melting point 76° C.

Similarly, it is possible to prepare for example the following compounds of the formula (II):
4-methyl-2-methoxycarbonyl-thiophene-3-sulphonamide (mp.: 54° C.),
4-methyl-2-ethoxycarbonyl-thiophene-3-sulphonamide (mp.: 65° C.),
4-methyl-2-n-propoxycarbonyl-thiophene-3-sulphonamide (mp.: 90° C.),
4-methyl-2-(oxetan-2-yl-oxycarbonyl)-thiophene-3-sulphonamide,
4-ethyl-2-methoxycarbonyl-thiophene-3-sulphonamide,
4-ethyl-2-ethoxycarbonyl-thiophene-3-sulphonamide,
4-ethyl-2-n-propoxycarbonyl-thiophene-3-sulphonamide,
4-ethyl-2-i-propoxycarbonyl-thiophene-3-sulphonamide,
4-ethyl-2-(oxetan-2-yl-oxycarbonyl)-thiophene-3-sulphonamide,
4-fluoro-2-methoxycarbonyl-thiophene-3-sulphonamide,
4-fluoro-2-ethoxycarbonyl-thiophene-3-sulphonamide,
4-fluoro-2-n-propoxycarbonyl-thiophene-3-sulphonamide,
4-fluoro-2-i-propoxycarbonyl-thiophene-3-sulphonamide,
4-fluoro-2-(oxetan-2-yl-oxycarbonyl)-thiophene-3-sulphonamide,
4chloro-2-methoxycarbonyl-thiophene-3-sulphonamide,
4-chloro-2-ethoxycarbonyl-thiophene-3-sulphonamide,
4-chloro-2-n-propoxycarbonyl-thiophene-3-sulphonamide,
4-chloro-2-i-propoxycarbonyl-thiophene-3-sulphonamide,
4-chloro-2-(oxetan-2-yl-oxycarbonyl)-thiophene-3-sulphonamide,
4-bromo-2-methoxycarbonyl-thiophene-3-sulphonamide,
4-bromo-2-ethoxycarbonyl-thiophene-3-sulphonamide,
4-bromo-2-n-propoxycarbonyl-thiophene-3-sulphonamide,
4-bromo-2-i-propoxycarbonyl-thiophene-3-sulphonamide,
4-bromo-2-(oxetan-2-yl-oxycarbonyl)-thiophene-3-sulphonamide,
4-methoxy-2-methoxycarbonyl-thiophene-3-sulphonamide,
4-methoxy-2-ethoxycarbonyl-thiophene-3-sulphonamide,
4-methoxy2n-propoxycarbonyl-thiophene3-sulphonamide,
4-methoxy-2-i-propoxycarbonyl-thiophene-3-sulphonamide,
4-methoxy-2-(oxetan-2-yl-oxycarbonyl)-thiophene-3-sulphonamide,
4-methylthio-2-methoxycarbonyl-thiophene-3-sulphonamide,
4-methylthio-2-ethoxycarbonyl-thiophene-3-sulphonamide,
4-methylthio-2-n-propoxycarbonyl-thiophene-3-sulphonamide,
4-methylthio-2-i-propoxycarbonyl-thiophene-3-sulphonamide,
4-methylthio-2-(oxetan-2-yl-oxycarbonyl)-thiophene-3-sulphonamide,
4-trifluoromethyl-2-methoxycarbonyl-thiophene-3-sulphonamide,
4-trifluoromethyl-2-ethoxycarbonyl-thiophene-3-sulphonamide,
4-trifluoromethyl-2-n-propoxycarbonyl-thiophene-3-sulphonamide,
4-trifluoromethyl-2-i-propoxycarbonyl-thiophene-3-sulphonamide,
4-trifluoromethyl-2-(oxetan-2-yl-oxycarbonyl)-thiophene-3-sulphonamide,
4-difluoromethoxy-2-methoxycarbonyl-thiophene-3-sulphonamide,
4-difluoromethoxy-2-ethoxycarbonyl-thiophene-3-sulphonamide,
4-difluoromethoxy-2-n-propoxycarbonyl-thiophene-3-sulphonamide,
4-difluoromethoxy-2-i-propoxycarbonyl-thiophene-3-sulphonamide,
4-difluoromethoxy-2-(oxetan-2-yl-oxycarbonyl)-thiophene-3-sulphonamide,
4-trifluoromethoxy-2-methoxycarbonyl-thiophene-3-sulphonamide,
4-trifluoromethoxy-2-ethoxycarbonyl-thiophene-3-sulphonamide,
4-trifluoromethoxy-2-n-propoxycarbonyl-thiophene-3-sulphonamide,
4-trifluoromethoxy-2-i-propoxycarbonyl-thiophene-3-sulphonamide,
4-trifluoromethoxy-2-(oxetan-2-yl-oxycarbonyl)-thiophene-3-sulphonamide.
6-methyl-2-methoxycarbonyl-benzenesulphonamide (mp.: 118° C.),
6-methyl-2-ethoxycarbonyl-benzenesulphonamide (mp.: 277° C.),
6-methyl-2-n-propoxycarbonyl-benzenesulphonamide,
6-methyl-2-i-propoxycarbonyl-benzenesulphonamide (mp.: 122° C.),
6-methyl-2-(oxetan-2-yl-oxycarbonyl)-benzenesulphonamide,
6-ethyl-2-methoxycarbonyl-benzenesulphonamide,
6-ethyl-2-ethoxycarbonyl-benzenesulphonamide,
6-ethyl-2-n-propoxycarbonyl-benzenesulphonamide,
6-ethyl-2-i-propoxycarbonyl-benzenesulphonamide,
6-ethyl-2-(oxetan-2-yl-oxycarbonyl)-benzenesulphonamide,
6-fluoro-2-methoxycarbonyl-benzenesulphonamide,
6-fluoro-2-ethoxycarbonyl-benzenesulphonamide,
6-fluoro-2-n-propoxycarbonyl-benzenesulphonamide,
6-fluoro-2-i-propoxycarbonyl-benzenesulphonamide,
6-fluoro-2-(oxetan-2-yl-oxycarbonyl)-benzenesulphonamide,
6-chloro-2-methoxycarbonyl-benzenesulphonamide,
6-chloro-2-ethoxycarbonyl-benzenesulphonamide,
6-chloro-2-n-propoxycarbonyl-benzenesulphonamide,
6-chloro-2-i-propoxycarbonyl-benzenesulphonamide,
6-chloro-2-(oxetan-2-yl-oxycarbonyl)-benzenesulphonamide,
6-bromo-2-methoxycarbonyl-benzenesulphonamide,
6-bromo-2-ethoxycarbonyl-benzenesulphonamide,
6-bromo-2-n-propoxycarbonyl-benzenesulphonamide, 6-bromo-2-i-propoxycarbonyl-benzenesulphonamide,
6-bromo-2-(oxetan-2-yl-oxycarbonyl)-benzenesulphonamide,
6-methoxy-2-methoxycarbonyl-benzenesulphonamide,
6-methoxy-2-ethoxycarbonyl-benzenesulphonamide,
6-methoxy-2-n-propoxycarbonyl-benzenesulphonamide,
6-methoxy-2-i-propoxycarbonyl-benzenesulphonamide,
6-methoxy-2-(oxetan-2-yl-oxycarbonyl)-benzenesulphonamide,
6-methylthio-2-methoxycarbonyl-benzenesulphonamide,
6-methylthio-2-ethoxycarbonyl-benzenesulphonamide,
6-methylthio-2-n-propoxycarbonyl-benzenesulphonamide,
6-methylthio-2-i-propoxycarbonyl-benzenesulphonamide,
6-methylthio-2-(oxetan-2-yl-oxycarbonyl)-benzenesulphonamide,
6-trifluoromethyl-2-methoxycarbonyl-benzenesulphonamide,
6-trifluoromethyl-2-ethoxycarbonyl-benzenesulphonamide,
6-trifluoromethyl-2-n-propoxycarbonyl-benzenesulphonamide,
6-trifluoromethyl-2-i-propoxycarbonyl-benzenesulphonamide,
6-trifluoromethyl-2-(oxetan-2-yl-oxycarbonyl)-benzenesulphonamide,
6-difluoromethoxy-2-methoxycarbonyl-benzenesulphonamide,
6-difluoromethoxy-2-ethoxycarbonyl-benzenesulphonamide,
6-difluoromethoxy-2-n-propoxycarbonyl-benzenesulphonamide,
6-difluoromethoxy-2-i-propoxycarbonyl-benzenesulphonamide,
6-difluoromethoxy-2-(oxetan-2-yl-oxycarbonyl)-benzenesulphonamide,
6-trifluoromethoxy-2-methoxycarbonyl-benzenesulphonamide,
6-trifluoromethoxy-2-ethoxycarbonyl-benzenesulphonamide,
6-trifluoromethoxy-2-n-propoxycarbonyl-benzenesulphonamide,
6-trifluoromethoxy-2-i-propoxycarbonyl-benzenesulphonamide,
6-trifluoromethoxy-2-(oxetan-2-yl-oxycarbonyl)-benzenesulphonamide.

Starting Materials of the Formula (IV)

Example (IV-1)

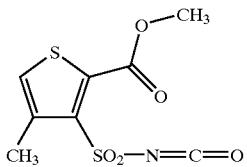

A mixture of 25 g (95 mmol) of 4-methyl-2-methoxycarbonyl-thiophene-3-sulphonamide, 9.4 g (95 mmol) of n-butyl isocyanate and 100 ml of chlorobenzene is heated to boiling point, and at reflux temperature, phosgene is introduced for 4 hours. The mixture is subsequently concentrated using water pump vacuum and the residue is purified by distillation under reduced pressure (2 mbar).

11 g (40% of theory) of 4-methyl-2-methoxycarbonyl-thiophen-3-yl-sulfonyl isocyanate of a boiling range of 140° C.–145° C. (at 2 mbar), which solidify to give colourless crystals, are obtained.

Similarly, it is possible to prepare for example the following compounds of the formula (II):
4-methyl-2-ethoxycarbonyl-thiophen-3-yl-sulphonyl isocyanate,
4-methyl-2-n-propoxycarbonyl-thiophen-3-yl-sulphonyl isocyanate,
4-methyl-2-i-propoxycarbonyl-thiophen-3-yl-sulphonyl isocyanate,
4-methyl-2-(oxetan-2-yl-oxycarbonyl)-thiophen-3-yl-sulphonyl isocyanate,
4-ethyl-2-methoxycarbonyl-thiophen-3-yl-sulphonyl isocyanate,
4-ethyl-2-ethoxycarbonyl-thiophen-3-yl-sulphonyl isocyanate,
4-ethyl-2-n-propoxycarbonyl-thiophen-3-yl-sulphonyl isocyanate,
4-ethyl-2-i-propoxycarbonyl-thiophen-3-yl-sulphonyl isocyanate,
4-ethyl-2-(oxetan-2-yl-oxycarbonyl)-thiophen-3-yl-sulphonyl isocyanate,
4-fluoro-2-methoxycarbonyl-thiophen-3-yl-sulphonyl isocyanate,
4-fluoro-2-ethoxycarbonyl-thiophen-3-yl-sulphonyl isocyanate,
4-fluoro-2-n-propoxycarbonyl-thiophen-3-yl-sulphonyl isocyanate,
4-fluoro-2-i-propoxycarbonyl-thiophen-3-yl-sulphonyl isocyanate,
4-fluoro-2-(oxetan-2-yl-oxycarbonyl)-thiophen-3-yl-sulphonyl isocyanate,
4-chloro-2-methoxycarbonyl-thiophen-3-yl-sulphonyl isocyanate,
4-chloro-2-ethoxycarbonyl-thiophen-3-yl-sulphonyl isocyanate,
4-chloro-2-n-propoxycarbonyl-thiophen-3-yl-sulphonyl isocyanate,
4-chloro-2-i-propoxycarbonyl-thiophen-3-yl-sulphonyl isocyanate,
4-chloro-2-(oxetan-2-yl-oxycarbonyl)-thiophen-3-yl-sulphonyl isocyanate,
4-bromo-2-methoxycarbonyl-thiophen-3-yl-sulphonyl isocyanate,
4-bromo-2-ethoxycarbonyl-thiophen-3-yl-sulphonyl isocyanate,
4-bromo-2-n-propoxycarbonyl-thiophen-3-yl-sulphonyl isocyanate,
4-bromo-2-i-propoxycarbonyl-thiophen-3-yl-sulphonyl isocyanate,
4-bromo-2-(oxetan-2-yl-oxycarbonyl)-thiophen-3-yl-sulphonyl isocyanate,
4-methoxy-2-methoxycarbonyl-thiophen-3-yl-sulphonyl isocyanate,
4-methoxy-2-ethoxycarbonyl-thiophen-3-yl-sulphonyl isocyanate,
4-methoxy-2-n-propoxycarbonyl-thiophen-3-yl-sulphonyl isocyanate,
4-methoxy-2-i-propoxycarbonyl-thiophen-3-yl-sulphonyl isocyanate,
4-methoxy-2-(oxetan-2-yl-oxycarbonyl)-thiophen-3-yl-sulphonyl isocyanate,
4-methylthio-2-methoxycarbonyl-thiophen-3-yl-sulphonyl isocyanate,
4-methylthio-2-ethoxycarbonyl-thiophen-3-yl-sulphonyl isocyanate,
4-methylthio-2-n-propoxycarbonyl-thiophen-3-yl-sulphonyl isocyanate,
4-methylthio-2-i-propoxycarbonyl-thiophen-3-yl-sulphonyl isocyanate, 4-methylthio-2-(oxetan-2-yl-oxycarbonyl)-thiophen-3-yl-sulphonyl isocyanate,
4-trifluoromethyl-2-methoxycarbonyl-thiophen-3-yl-sulphonyl isocyanate,
4-trifluoromethyl-2-ethoxycarbonyl-thiophen-3-yl-sulphonyl isocyanate,
4-trifluoromethyl-2-n-propoxycarbonyl-thiophen-3-yl-sulphonyl isocyanate,
4-trifluoromethyl-2-i-propoxycarbonyl-thiophen-3-yl-sulphonyl isocyanate,
4-trifluoromethyl-2-(oxetan-2-yl-oxycarbonyl)-thiophen-3-yl-sulphonyl isocyanate,
4-difluoromethoxy-2-methoxycarbonyl-thiophen-3-yl-sulphonyl isocyanate,
4-difluoromethoxy-2-ethoxycarbonyl-thiophen-3-yl-sulphonyl isocyanate,
4-difluoromethoxy-2-n-propoxycarbonyl-thiophen-3-yl-sulphonyl isocyanate,
4-difluoromethoxy-2-i-propoxycarbonyl-thiophen-3-yl-sulphonyl isocyanate,
4-difluoromethoxy-2-(oxetan-2-yl-oxycarbonyl)-thiophen-3-yl-sulphonyl isocyanate,
4-trifluoromethoxy-2-methoxycarbonyl-thiophen-3-yl-sulphonyl isocyanate,
4-trifluoromethoxy-2-ethoxycarbonyl-thiophen-3-yl-sulphonyl isocyanate,
4-trifluoromethoxy-2-n-propoxycarbonyl-thiophen-3-yl-sulphonyl isocyanate,
4-trifluoromethoxy-2-i-propoxycarbonyl-thiophen-3-yl-sulphonyl isocyanate,
4-trifluoromethoxy-2-(oxetan-2-yl-oxycarbonyl)-thiophen-3-yl-sulphonyl isocyanate,
6-methyl-2-methoxycarbonyl-phenylsulphonyl isocyanate,
6-methyl-2-ethoxycarbonyl-phenylsulphonyl isocyanate,
6-methyl-2-n-propoxycarbonyl-phenylsulphonyl isocyanate,
6-methyl -2-i-propoxycarbonyl-phenylsulphonyl isocyanate,
6-methyl-2-(oxetan-2-yl -oxycarbonyl)-phenylsulphonyl isocyanate,
6-ethyl-2-methoxycarbonyl-phenylsulphonyl isocyanate,
6-ethyl-2-ethoxycarbonyl-phenylsulphonyl isocyanate,
6-ethyl-2-n-propoxycarbonyl-phenylsulphonyl isocyanate,
6-ethyl-2-i-propoxycarbonyl-phenylsulphonyl isocyanate,
6-ethyl-2-(oxetan-2-yl-oxycarbonyl)-phenylsulphonyl isocyanate,
6-fluoro-2-methoxycarbonyl-phenylsulphonyl isocyanate,
6-fluoro-2-ethoxycarbonyl-phenylsulphonyl isocyanate,
6-fluoro-2-n-propoxycarbonyl-phenylsulphonyl isocyanate,
6-fluoro-2-i-propoxycarbonyl-phenylsulphonyl isocyanate,
6-fluoro-2-(oxetan-2-yl-oxycarbonyl)-phenylsulphonyl isocyanate,
6-chloro-2-methoxycarbonyl-phenylsulphonyl isocyanate,
6-chloro-2-ethoxycarbonyl-phenylsulphonyl isocyanate,
6-chloro-2-n-propoxycarbonyl-phenylsulphonyl isocyanate,
6-chloro-2-i-propoxycarbonyl-phenylsulphonyl isocyanate,
6-chloro-2-(oxetan-2-yl-oxycarbonyl)-phenylsulphonyl isocyanate,
6-bromo-2-methoxycarbonyl-phenylsulphonyl isocyanate,
6-bromo-2-ethoxycarbonyl-phenylsulphonyl isocyanate,
6-bromo-2-n-propoxycarbonyl-phenylsulphonyl isocyanate,
6-bromo-2-i-propoxycarbonyl-phenylsulphonyl isocyanate,
6-bromo-2-(oxetan-2-yl-oxycarbonyl)-phenylsulphonyl isocyanate,
6-methoxy-2-methoxycarbonyl-phenylsulphonyl isocyanate,
6-methoxy-2-ethoxycarbonyl- phenylsulphonyl isocyanate,
6-methoxy-2-n-propoxycarbonyl-phenylsulphonyl isocyanate,
6-methoxy-2-i-propoxycarbonyl-phenylsulphonyl isocyanate,
6-methoxy-2-(oxetan-2-yl-oxycarbonyl)-phenylsulphonyl isocyanate,
6-methylthio-2-methoxycarbonyl-phenylsulphonyl isocyanate,
6-methylthio-2-ethoxycarbonyl-phenylsulphonyl isocyanate,
6-methylthio-2-n-propoxycarbonyl-phenylsulphonyl isocyanate,
6-methylthio-2-i-propoxycarbonyl-phenylsulphonyl isocyanate,
6-methylthio-2-(oxetan-2-yl-oxycarbonyl)-phenylsulphonyl isocyanate,
6-trifluoromethyl-2-methoxycarbonyl-phenylsulphonyl isocyanate,
6-trifluoromethyl-2-ethoxycarbonyl-phenylsulphonyl isocyanate,
6-trifluoromethyl-2-n-propoxycarbonyl-phenylsulphonyl isocyanate,
6-trifluoromethyl -2-i-propoxycarbonyl-phenylsulphonyl isocyanate,
6-trifluoromethyl-2-(oxetan-2-yl-oxycarbonyl)-phenylsulphonyl isocyanate,
6-difluoromethoxy-2-methoxycarbonyl-phenylsulphonyl isocyanate,
6-difluoromethoxy-2-ethoxycarbonyl-phenylsulphonyl isocyanate,
6-difluoromethoxy-2-n-propoxycarbonyl-phenylsulphonyl isocyanate,
6-difluoromethoxy-2-i-propoxycarbonyl-phenylsulphonyl isocyanate,
6-difluoromethoxy-2-(oxetan-2-yl-oxycarbonyl)-phenylsulphonyl isocyanate,
6-trifluoromethoxy-2-methoxycarbonyl-phenylsulphonyl isocyanate,
6-trifluoromethoxy-2-ethoxycarbonyl-phenylsulphonyl isocyanate,
6-trifluoromethoxy-2-n-propoxycarbonyl-phenylsulphonyl isocyanate,
6-trifluoromethoxy-2-i-propoxycarbonyl-phenylsulphonyl isocyanate,
6-trifluoromethoxy-2-(oxetan-2-yl-oxycarbonyl)-phenylsulphonyl isocyanate.

Starting Materials of the Formula (VI)

Example (VI-1)

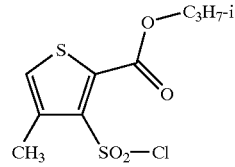

A solution of 21.2 g (90 mmol) of i-propyl 3-amino-4-methyl-thiophene-2-carboxylate hydrochloride in 60 ml of conc. hydrochloric acid is cooled to about −10° C., and a solution of 6.9 g (100 mmol) of sodium nitrite in 13 ml of water is then added dropwise with stirring to this mixture at −10° C. to −5° C. The reaction mixture is stirred at −5° C. to 0° C. for about 60 minutes. The resulting diazonium salt solution is added dropwise at about 15° C. to a solution of 50 g of sulphur dioxide in 110 ml of acetic acid containing 10 ml of a saturated aqueous solution of copper(II) chloride. The mixture is stirred at room temperature (about 20° C.) for 12 hours and then diluted with about 500 ml of methylene chloride, washed twice with ice-water, dried over magnesium sulphate and filtered. The filtrate is concentrated using water pump vacuum, the residue is digested with petroleum ether and the resulting crystalline product is isolated by filtration with suction.

17.0 g of (67% of theory) of 4-methyl-2-i-propoxycarbonyl-thiophene-3-sulphonyl chloride are obtained as a yellow solid of melting point 58° C.

Similarly, it is possible to prepare for example the following compounds of the formula (VI):
4-methyl-2-methoxycarbonyl-thiophene-3-sulphonyl chloride (mp.: 56° C.),
4-methyl-2-ethoxycarbonyl-thiophene-3-sulphonyl chloride (mp.: 47° C.),
4-methyl-2-n-propoxycarbonyl-thiophene-3-sulphonyl chloride (mp.: 42° C.),
4-methyl-2-(oxetan-2-yl-oxycarbonyl)-thiophene-3-sulphonyl chloride,
4-ethyl-2-methoxycarbonyl-thiophene-3-sulphonyl chloride,
4-ethyl-2-ethoxycarbonyl-thiophene-3-sulphonyl chloride,
4-ethyl-2-n-propoxycarbonyl-thiophene-3-sulphonyl chloride,
4-ethyl-2-i-propoxycarbonyl-thiophene-3-sulphonyl chloride,
4-ethyl-2-(oxetan-2-yl-oxycarbonyl)-thiophene-3-sulphonyl chloride,
4-fluoro-2-methoxycarbonyl-thiophene-3-sulphonyl chloride,
4-fluoro-2-ethoxycarbonyl-thiophene-3-sulphonyl chloride,
4-fluoro-2-n-propoxycarbonyl-thiophene-3-sulphonyl chloride,
4-fluoro-2-i-propoxycarbonyl-thiophene-3-sulphonyl chloride,
4-fluoro-2-(oxetan-2-yl-oxycarbonyl)-thiophene-3-sulphonyl chloride,
4-chloro-2-methoxycarbonyl-thiophene-3-sulphonyl chloride,
4-chloro-2-ethoxycarbonyl-thiophene-3-sulphonyl chloride,
4-chloro-2-n-propoxycarbonyl-thiophene-3-sulphonyl chloride,
4-chloro-2-i-propoxycarbonyl-thiophene-3-sulphonyl chloride,
4-chloro-2-(oxetan-2-yl-oxycarbonyl)-thiophene-3-sulphonyl chloride,
4-bromo-2-methoxycarbonyl-thiophene-3-sulphonyl chloride,
4-bromo-2-ethoxycarbonyl-thiophene-3-sulphonyl chloride,
4-bromo-2-n-propoxycarbonyl-thiophene-3-sulphonyl chloride,
4-bromo-2-i-propoxycarbonyl-thiophene-3-sulphonyl chloride,
4-bromo-2-(oxetan-2-yl-oxycarbonyl)-thiophene-3-sulphonyl chloride,
4-methoxy-2-methoxycarbonyl-thiophene-3-sulphonyl chloride,
4-methoxy-2-ethoxycarbonyl-thiophene-3-sulphonyl chloride,
4-methoxy-2-n-propoxycarbonyl-thiophene-3-sulphonyl chloride,
4-methoxy-2-i-propoxycarbonyl-thiophene-3-sulphonyl chloride,
4-methoxy-2-(oxetan-2-yl-oxycarbonyl)-thiophene-3-sulphonyl chloride,
4-methylthio-2-methoxycarbonyl-thiophene-3-sulphonyl chloride,
4-methylthio-2-ethoxycarbonyl-thiophene-3-sulphonyl chloride,
4-methylthio-2-n-propoxycarbonyl-thiophene-3-sulphonyl chloride,
4-methylthio-2-i-propoxycarbonyl-thiophene-3-sulphonyl chloride,
4-methylthio-2-(oxetan-2-yl-oxycarbonyl)-thiophene-3-sulphonyl chloride,
4-trifluoromethyl-2-methoxycarbonyl-thiophene-3-sulphonyl chloride,
4-trifluoromethyl-2-ethoxycarbonyl-thiophene-3-sulphonyl chloride,
4-trifluoromethyl-2-n-propoxycarbonyl-thiophene-3-sulphonyl chloride,
4-trifluoromethyl-2-i-propoxycarbonyl-thiophene-3-sulphonyl chloride,
4-trifluoromethyl-2-(oxetan-2-yl-oxycarbonyl)-thiophene-3-sulphonyl chloride,
4-difluoromethoxy-2-methoxycarbonyl-thiophene-3-sulphonyl chloride,
4-difluoromethoxy-2-ethoxycarbonyl-thiophene-3-sulphonyl chloride,
4-difluoromethoxy-2-n-propoxycarbonyl-thiophene-3-sulphonyl chloride,
4-difluoromethoxy-2-i-propoxycarbonyl-thiophene-3-sulphonyl chloride,
4-difluoromethoxy-2-(oxetan-2-yl-oxycarbonyl)-thiophene-3-sulphonyl chloride,
4-trifluoromethoxy-2-methoxycarbonyl-thiophene-3-sulphonyl chloride,
4-trifluoromethoxy-2-ethoxycarbonyl-thiophene-3-sulphonyl chloride,
4-trifluoromethoxy-2-n-propoxycarbonyl-thiophene-3-sulphonyl chloride,
4-trifluoromethoxy-2-i-propoxycarbonyl-thiophene-3-sulphonyl chloride,
4-trifluoromethoxy-2-(oxetan-2-yl-oxycarbonyl)-thiophene-3-sulphonyl chloride.
6-methyl-2-methoxycarbonyl-benzenesulphonyl chloride (mp.: 109° C.),
6-methyl-2-ethoxycarbonyl-benzenesulphonyl chloride (mp.: 82° C.),
6-methyl-2-n-propoxycarbonyl-benzenesulphonyl chloride (mp.: 52° C.),
6-methyl-2-i-propoxycarbonyl-benzenesulphonyl chloride (mp.: 51° C.),
6-methyl-2-(oxetan-2-yl-oxycarbonyl)-benzenesulphonyl chloride,
6-ethyl-2-methoxycarbonyl-benzenesulphonyl chloride,
6-ethyl-2-ethoxycarbonyl-benzenesulphonyl chloride,
6-ethyl-2-n-propoxycarbonyl-benzenesulphonyl chloride,
6-ethyl-2-i-propoxycarbonyl-benzenesulphonyl chloride,
6-ethyl-2-(oxetan-2-yl-oxycarbonyl)-benzenesulphonyl chloride,
6-fluoro-2-methoxycarbonyl-benzenesulphonyl chloride,
6-fluoro-2-ethoxycarbonyl-benzenesulphonyl chloride,
6-fluoro-2-n-propoxycarbonyl-benzenesulphonyl chloride,
6-fluoro-2-i-propoxycarbonyl-benzenesulphonyl chloride,
6-fluoro-2-(oxetan-2-yl-oxycarbonyl)-benzenesulphonyl chloride,
6-chloro-2-methoxycarbonyl-benzenesulphonyl chloride,
6-chloro-2-ethoxycarbonyl-benzenesulphonyl chloride,
6-chloro-2-n-propoxycarbonyl-benzenesulphonyl chloride,
6-chloro-2-i-propoxycarbonyl-benzenesulphonyl chloride,
6-chloro-2-(oxetan-2-yl-oxycarbonyl)-benzene-sulphonyl chloride, 6-bromo-2-methoxycarbonyl-benzenesulphonyl chloride,
6-bromo-2-ethoxycarbonyl-benzenesulphonyl chloride,
6-bromo-2-n-propoxycarbonyl-benzenesulphonyl chloride,
6-bromo-2-i-propoxycarbonyl-benzenesulphonyl chloride,
6-bromo-2-(oxetan-2-yl-oxycarbonyl)-benzenesulphonyl chloride,
6-methoxy-2-methoxycarbonyl-benzenesulphonyl chloride,
6-methoxy-2-ethoxycarbonyl-benzenesulphonyl chloride,
6-methoxy-2-n-propoxycarbonyl-benzenesulphonyl chloride,
6-methoxy-2-i-propoxycarbonyl-benzenesulphonyl chloride,
6-methoxy-2-(oxetan-2-yl-oxycarbonyl)-benzenesulphonyl chloride,
6-methylthio-2-methoxycarbonyl-benzenesulphonyl chloride,
6-methylthio-2-ethoxycarbonyl-benzenesulphonyl chloride,
6-methylthio-2-n-propoxycarbonyl-benzenesulphonyl chloride,
6-methylthio-2-i-propoxycarbonyl-benzenesulphonyl chloride,
6-methylthio-2-(oxetan-2-yl-oxycarbonyl)-benzenesulphonyl chloride,
6-trifluoromethyl-2-methoxycarbonyl-benzenesulphonyl chloride,
6-trifluoromethyl-2-ethoxycarbonyl-benzenesulphonyl chloride (amorphous),
6-trifluoromethyl-2-n-propoxycarbonyl-benzenesulphonyl chloride,
6-trifluoromethyl-2-i-propoxycarbonyl-benzenesulphonyl chloride (mp.: 64° C.),
6-trifluoromethyl-2-(oxetan-2-yl-oxycarbonyl)-benzenesulphonyl chloride,
6-difluoromethoxy-2-methoxycarbonyl-benzenesulphonyl chloride,
6-difluoromethoxy-2-ethoxycarbonyl-benzenesulphonyl chloride,
6-difluoromethoxy-2-n-propoxycarbonyl-benzenesulphonyl chloride,
6-difluoromethoxy-2-i-propoxycarbonyl-benzenesulphonyl chloride,
6-difluoromethoxy-2-(oxetan-2-yl-oxycarbonyl)-benzenesulphonyl chloride,
6-trifluoromethoxy-2-methoxycarbonyl-benzenesulphonyl chloride,
6-trifluoromethoxy-2-ethoxycarbonyl-benzenesulphonyl chloride,
6-trifluoromethoxy-2-n-propoxycarbonyl-benzenesulphonyl chloride,
6-trifluoromethoxy-2-i-propoxycarbonyl-benzenesulphonyl chloride,
6-trifluoromethoxy-2-(oxetan-2-yl-oxycarbonyl)-benzenesulphonyl chloride.

Starting Materials of the Formula (X)

Example (X-1)

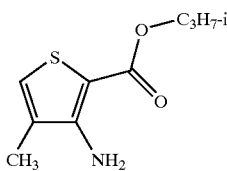

Step 1

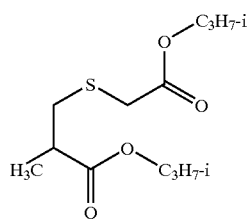

With shaking, a mixture of 192 g (1.43 mol) of i-propyl mercaptoacetate and 183 g (1.43 mol) of i-propyl methacrylate is admixed with 5 drops of piperidine. The mixture is heated to 50° C., admixed with a further 20 drops of piperidine and stirred at a bath temperature of 100° C. for 12 hours. The mixture is subsequently distilled under reduced pressure.

288 g (77% of theory) of i-propyl 2-methyl-3-(i-propoxycarbonylmethylthio)-propionate are obtained as a colourless oil of a boiling range of 135° C. to 140° C. at 2 mbar.

Similarly, it is possible to prepare for example the following compounds:
methyl 2-methyl-3-(methoxycarbonylmethylthio)-propionate,
ethyl 2-methyl-3-(ethoxycarbonylmethylthio)-propionate (bp.: 105° C. to 112° C. at 1 mbar),
n-propyl 2-methyl-3-(n-propoxycarbonylmethylthio)-propionate (bp.: 145° C. to 147° C. at 3 mbar),
methyl 2-methyl-3-(ethoxycarbonylmethylthio)-propionate (bp.: 150° C. to 152° C. at 0.1 mbar),
methyl 2-methyl-3-(n-propoxycarbonylmethylthio)-propionate (bp.: 158° C. to 160° C. at 0.1 mbar),
methyl 2-methyl-3-(i-propoxycarbonylmethylthio)-propionate (bp.: 162° C. to 165° C. at 0.1 mbar),
methyl 2-ethyl-3-(methoxycarbonylmethylthio)-propionate,
ethyl 2-ethyl-3-(ethoxycarbonylmethylthio)-propionate,
n-propyl 2-ethyl-3-(n-propoxycarbonylmethylthio)-propionate,
i-propyl 2-ethyl-3-(i-propoxycarbonylmethylthio)-propionate,
methyl 2-ethyl-3-(ethoxycarbonylmethylthio)-propionate,
methyl 2-ethyl-3-(n-propoxycarbonylmethylthio)-propionate,
methyl 2-ethyl-3-(i-propoxycarbonylmethylthio)-propionate,
methyl 2-trifluoromethyl-3-(methoxycarbonylmethylthio)-propionate,
ethyl 2-trifluoromethyl-3-(ethoxycarbonylmethylthio)-propionate,
n-propyl 2-trifluoromethyl-3-(n-propoxycarbonylmethylthio)-propionate,
i-propyl 2-trifluoromethyl-3-(i-propoxycarbonylmethylthio)-propionate,
methyl 2-trifluoromethyl-3-(ethoxycarbonylmethylthio)-propionate,
methyl 2-trifluoromethyl-3-(n-propoxycarbonylmethylthio)-propionate,
methyl 2-trifluoromethyl-3-(i-propoxycarbonylmethylthio)-propionate,
methyl 2-chloro-3-(methoxycarbonylmethylthio)-propionate,
ethyl 2-chloro-3-(ethoxycarbonylmethylthio)-propionate,
n-propyl 2-chloro-3-(n-propoxycarbonylmethylthio)-propionate,
i-propyl 2-chloro-3-(i-propoxycarbonylmethylthio)-propionate, methyl 2-chloro-3-(ethoxycarbonylmethylthio)-propionate,
methyl 2-chloro-3-(n-propoxycarbonylmethylthio)-propionate,
methyl 2-chloro-3-(i-propoxycarbonylmethylthio)-propionate.

Step 2

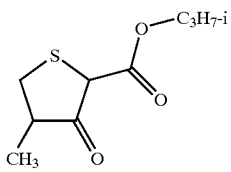

At room temperature (about 20° C.), 480 g (1.83 mol) of i-propyl 2-methyl-3-(i-propoxycarbonylmethylthio)-propionate are added dropwise to a suspension of 246 g (3.0 mol) of sodium i-propoxide in 1 litre of toluene, and the mixture is then stirred at about 90° C. for about 12 hours. The mixture is subsequently poured into ice-cold 2N hydrochloric acid. This mixture is then extracted three times with diethyl ether and the combined extracts are washed twice with water. The organic phase is dried over magnesium sulphate and filtered. The filtrate is concentrated using water pump vacuum and the residue is distilled under reduced pressure.

254 g (69% of theory) of i-propyl 4-methyl-3-oxo-tetrahydrothiophene-2-carboxylate are obtained as a light-yellow oil of boiling point 119° C. to 120° C. at 1 mbar.

Similarly, it is possible to prepare for example the following compounds:
methyl 4-methyl-3-oxo-tetrahydrothiophene-2-carboxylate,
ethyl 4-methyl-3-oxo-tetrahydrothiophene-2-carboxylate (bp.: 112° C. at 4 mbar),
n-propyl 4-methyl-3-oxo-tetrahydrothiophene-2-carboxylate (bp.: 127° C. to 128° C. at 1 mbar),
methyl 4-ethyl-3-oxo-tetrahydrothiophene-2-carboxlate,
ethyl 4-ethyl-3-oxo-tetrahydrothiophene-2-carboxylate,
n-propyl 4-ethyl-3-oxo-tetrahydrothiophene-2-carboxylate,
i-propyl 4-ethyl-3-oxo-tetrahydrothiophene-2-carboxylate,
methyl 4-trifluoromethyl-3-oxo-tetrahydrothiophene-2-carboxylate,
ethyl 4-trifluoromethyl-3-oxo-tetrahydrothiophene-2-carboxylate,
n-propyl 4-trifluoromethyl-3-oxo-tetrahydrothiophene-2-carboxylate,
i-propyl 4-trifluoromethyl-3-oxo-tetrahydrothiophene-2-carboxylate,
methyl 4-chloro-3-oxo-tetrahydrothiophene-2-carboxylate,
ethyl 4-chloro-3-oxo-tetrahydrothiophene-2-carboxylate,
n-propyl 4-chloro-3-oxo-tetrahydrothiophene-2-carboxylate,
i-propyl 4-chloro-3-oxo-tetrahydrothiophene-2-carboxylate.

Step 3

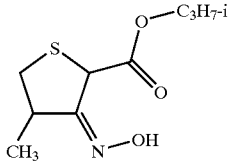

A mixture of 505 g (2.5 mol) of i-propyl 4-methyl-3-oxo-tetrahydrothiophene-2-carboxylate, 497 g (7.2 mol) of hydroxylamine hydrochloride, 753 g (3.8 mol) of barium carbonate and 2.5 litres of isopropanol is heated under reflux for about 12 hours. The mixture is subsequently filtered off with suction, the filter cake is washed with hot isopropanol and the filtrate is concentrated using water pump vacuum. The residue is taken up in 2 litres of diethyl ether, washed twice with water, dried over magnesium sulphate and filtered. The solvent is carefully distilled off from the filtrate using water pump vacuum.

445 g (82% of theory) of i-propyl 4-methyl-3-hydroximino-tetrahydrothiophene-2-carboxylate are obtained as a light-yellow oily crude product which is employed without any further purification for the next step.

Similarly, it is possible to prepare for example the following compounds:
methyl 4-methyl-3-hydroximino-tetrahydrothiophene-2-carboxylate,
ethyl 4-methyl-3-hydroximino-tetrahydrothiophene-2-carboxylate (colourless oil),
n-propyl 4-methyl-3-hydroximino-tetrahydrothiophene-2-carboxylate (light-yellow oil),
methyl 4-ethyl-3-hydroximino-tetrahydrothiophene-2-carboxylate,
ethyl 4-ethyl-3-hydroximino-tetrahydrothiophene-2-carboxylate,
n-propyl 4-ethyl-3-hydroximino-tetrahydrothiophene-2-carboxylate,
i-propyl 4-ethyl-3-hydroximino-tetrahydrothiophene-2-carboxylate,
methyl 4-trifluoromethyl-3-hydroximino-tetrahydrothiophene-2-carboxylate,
ethyl 4-trifluoromethyl-3-hydroximino-tetrahydrothiophene-2-carboxylate,
n-propyl 4-trifluoromethyl-3-hydroximino-tetrahydrothiophene-2-carboxylate,
i-propyl 4-trifluoromethyl-3-hydroximino-tetrahydrothiophene-2-carboxylate,
methyl 4-chloro-3-hydroximino-tetrahydrothiophene-2-carboxylate,
ethyl 4-chloro-3-hydroximino-tetrahydrothiophene-2-carboxylate,
n-propyl 4-chloro-3-hydroximino-tetrahydrothiophene-2-carboxylate,
i-propyl 4-chloro-3-hydroximino-tetrahydrothiophene-2-carboxylate.

Step 4

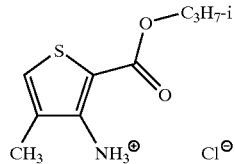

334 g (1.54 mol) of i-propyl 4-methyl-3-hydroximino-tetrahydrothiophene-2-carboxylate are dissolved in 5 litres of methyl tert-butyl ether and cooled using an ice bath. Hydrogen chloride is then—after the ice bath had been removed—introduced with stirring for two hours. The mixture is subsequently concentrated using water pump vacuum and the amorphous residue is crystallized from acetone.

358 g (99% of theory) of i-propyl 3-amino-4-methyl-thiophene-2-carboxylate hydrochloride are obtained as a beige-coloured solid of melting point 153° C.

Similarly, it is possible to prepare for example the following compounds:
ethyl 3-amino-4-methyl-thiophene-2-carboxylate hydrochloride (mp.: 133° C.),
n-propyl 3-amino-4-methyl-thiophene-2-carboxylate hydrochloride (mp.: 152° C.), ethyl 3-amino-4-ethyl-thiophene-2-carboxylate hydrochloride,
n-propyl 3-amino-4-ethyl-thiophene-2-carboxylate hydrochloride,
i-propyl 3-amino-4-ethyl-thiophene-2-carboxylate hydrochloride,
ethyl 3-amino-4-trifluoromethyl-thiophene-2-carboxylate hydrochloride,
n-propyl 3-amino-4-trifluoromethyl-thiophene-2-carboxylate hydrochloride,
i-propyl 3-amino-4-trifluoromethyl-thiophene-2-carboxylate hydrochloride,
ethyl 3-amino-4-chloro-thiophene-2-carboxylate hydrochloride,
n-propyl 3-amino-4-chloro-thiophene-2-carboxylate hydrochloride,
i-propyl 3-amino-4-chloro-thiophene-2-carboxylate hydrochloride.

Step 5

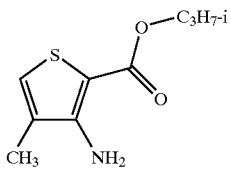

11.75 g (50 mmol) of i-propyl 3-amino-4-methyl-thiophene-2-carboxylate hydrochloride are dissolved in 100 ml of water. 150 ml of methylene chloride are added to this solution, and sodium bicarbonate is then added a little at a time until a pH of 7 has been exceeded. The mixture is stirred for 8 hours and the organic phase is separated off, washed with water, dried with magnesium sulphate and filtered. The filtrate is concentrated using water pump vacuum and the amorphous residue is crystallized from petroleum ether.

7.2 g (73% of theory) of i-propyl 3-amino-4-methyl-thiophene-2-carboxylate are obtained as a beige-coloured solid of melting point 40° C.

Similarly, it is possible to prepare for example the following compounds:
ethyl 3-amino-4-methyl-thiophene-2-carboxylate (mp.: 133° C.),
n-propyl 3-amino-4-methyl-thiophene-2-carboxylate (amorphous),
ethyl 3-amino-4-ethyl-thiophene-2-carboxylate,
n-propyl 3-amino-4-ethyl-thiophene-2-carboxylate,
i-propyl 3-amino-4-ethyl-thiophene-2-carboxylate,
ethyl 3-amino-4-trifluoromethyl-thiophene-2-carboxylate,
n-propyl 3-amino-4-trifluoromethyl-thiophene-2-carboxylate,
i-propyl 3-amino-4-trifluoromethyl-thiophene-2-carboxylate,
ethyl 3-amino-4-chloro-thiophene-2-carboxylate,
n-propyl 3-amino-4-chloro-thiophene-2-carboxylate,
i-propyl 3-amino-4-chloro-thiophene-2-carboxylate.

Use Examples

Example A

Pre-emergence Test

Solvent: 5 parts by weight of acetone
Emulsifier: 1 part by weight of alkylaryl polyglycol ether To produce a suitable preparation of the active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of active compound. Advantageously, the amount of water per unit area is kept constant. The active compound concentration in the preparation is not important, only the active compound appliation rate per unit area matters.

After three weeks, the degree of damage to the plants is rated in % damage in comparison to the development of the untreated control.

The figures denote:
0%=no action (like untreated control)
100%=total destruction In this test, very strong activity against weeds is shown, for example, by the compounds of Preparation Examples 1, 3, 5, 6, 7, 8, 9, 10, 12, 13, 16, 17, 18, 19, 20, 21, 22, 23, 28, 30, 31, 32, 33, 34, 35, 37, 38, 39, 40, 41, 42, 43, 44, 45, 46, 47, 48, 51, 53, 54, 55, 56, 57, 58, 59, 61, 62, 63, 64, 65, 66, 67, 68, 70, 72, 76, 77, 80, 81, 82, 84, 85, 86, 89, 93, 108, 121, 129, 130, 131, 134, 135, 136, 140, 141, 142, 143, 144, 145, 146, 147, 148, 149, 150, 151, 152, 153, 154, 155, 156, 157, 158, 159, 160, 161, 162, 163, 164, 165, 166, 167 and 172, combined with predominantly good tolerance by crop plants such as, for example, maize and soya beans.

"al."=active compound ("active ingredient")

TABLE A

Pre-emergence test/Greenhouse

| Active compound of Preparation Example | Application rate (g of ai./ha) | Maize | Soya beans | Lo-lium | Poa | Sor-ghum | Ambro-sia | Matri-caria | Sola-num |
|---|---|---|---|---|---|---|---|---|---|
| 5 | 30 | 0 | 20 | 95 | 95 | 90 | 95 | 95 | 95 |
| 1 | 30 | 10 | — | 95 | 95 | 90 | 95 | 95 | 95 |
| 6 | 125 | 0 | — | 95 | 95 | 95 | 95 | 95 | 95 |
| 7 | 60 | 0 | 0 | 95 | — | 95 | 95 | 95 | — |
| 8 | 60 | 30 | 0 | 95 | 90 | 80 | 90 | 95 | 95 |
| 9 | 125 | 0 | — | 80 | 80 | 60 | 95 | 90 | 95 |
| 10 | 250 | 0 | 20 | 80 | 90 | 70 | 95 | 95 | 95 |
| 12 | 125 | 0 | 0 | 80 | 80 | 60 | 95 | 95 | 95 |
| 13 | 125 | 30 | — | 90 | 80 | 70 | 95 | 95 | 90 |
| 16 | 30 | — | 0 | 95 | 95 | 90 | 95 | 95 | 95 |
| 17 | 30 | — | 0 | 80 | 95 | 60 | 95 | 95 | 95 |
| 18 | 60 | 10 | 0 | 80 | 95 | 90 | 95 | 95 | 95 |

TABLE A-continued

Pre-emergence test/Greenhouse

| Active compound of Preparation Example | Application rate (g of ai./ha) | Maize | Soya beans | Lo-lium | Poa | Sor-ghum | Ambro-sia | Matri-caria | Sola-num |
|---|---|---|---|---|---|---|---|---|---|
| 19 | 60 | 0 | 0 | 95 | 95 | — | 95 | 95 | 90 |
| 20 | 125 | 10 | 0 | 95 | 95 | 90 | 95 | 95 | 95 |
| 21 | 125 | 0 | 0 | 95 | 95 | 95 | 95 | 95 | 95 |
| 22 | 125 | 20 | 10 | 95 | 95 | 80 | 95 | 95 | 95 |
| 23 | 125 | 0 | 0 | — | 80 | 60 | 90 | 95 | 90 |
| 28 | 60 | 0 | — | 95 | 95 | 95 | 95 | 95 | 95 |
| 30 | 30 | 0 | — | 95 | 95 | 80 | 95 | 95 | 95 |
| 31 | 15 | 10 | — | 95 | 95 | 80 | 95 | 95 | 95 |
| 32 | 60 | 20 | 20 | 95 | 95 | 60 | 95 | 95 | 95 |
| 33 | 125 | 10 | — | — | 90 | 80 | 90 | 95 | 95 |
| 34 | 60 | 10 | 0 | 60 | 70 | 80 | 90 | 95 | 90 |
| 35 | 60 | 0 | — | 95 | 95 | 95 | 95 | 100 | 95 |
| 37 | 60 | 10 | 10 | 90 | 70 | — | 80 | 95 | 90 |
| 38 | 60 | 0 | — | 95 | 70 | 60 | 95 | 95 | 95 |
| 39 | 60 | 0 | 20 | 95 | 90 | — | 95 | 70 | 90 |
| 40 | 60 | 10 | 30 | 90 | 95 | — | 95 | 95 | 95 |
| 41 | 60 | 0 | — | 60 | 80 | 60 | 95 | 95 | 90 |
| 42 | 60 | 10 | 10 | 95 | 95 | — | 95 | 95 | 95 |
| 43 | 60 | — | 10 | 95 | 95 | 80 | 95 | 95 | 95 |
| 44 | 8 | 30 | 0 | 95 | 95 | 95 | 95 | 95 | 95 |
| 45 | 125 | 10 | 20 | 90 | 95 | — | 95 | 90 | 95 |
| 46 | 8 | 0 | — | 80 | 95 | 80 | 95 | 95 | 95 |
| 47 | 125 | 10 | 10 | 90 | 90 | 60 | 95 | 95 | 95 |
| 48 | 125 | 30 | 20 | 95 | 95 | — | 95 | 100 | 95 |
| 51 | 125 | 0 | 30 | 80 | 80 | 80 | 95 | 95 | 95 |
| 53 | 125 | 0 | — | 95 | 95 | — | 95 | 95 | 95 |
| 54 | 30 | 0 | — | 95 | 95 | 80 | 95 | 95 | 95 |
| 55 | 125 | 10 | — | 100 | 90 | 60 | 100 | 100 | 100 |
| 56 | 125 | — | 0 | 60 | 80 | — | — | 100 | 95 |
| 57 | 60 | 0 | — | 95 | 95 | 95 | — | 95 | 95 |
| 58 | 125 | 20 | — | 80 | 95 | — | — | 100 | 95 |
| 59 | 125 | 0 | — | 100 | 70 | — | 95 | 100 | 95 |
| 61 | 125 | 0 | — | 95 | 95 | 80 | 100 | 95 | 95 |
| 62 | 125 | 0 | — | 80 | 90 | 60 | — | 95 | 95 |
| 63 | 60 | 10 | — | 100 | 95 | 80 | 100 | 100 | 100 |
| 64 | 60 | 10 | 30 | 90 | 60 | — | 100 | 100 | 100 |
| 65 | 125 | 20 | — | 80 | 80 | 80 | — | 95 | 95 |
| 66 | 125 | 0 | — | 100 | — | 100 | — | 100 | 100 |
| 67 | 60 | 0 | — | 100 | — | 90 | — | 100 | 100 |
| 68 | 125 | 5 | 10 | 80 | 90 | 60 | 95 | 100 | 95 |
| 70 | 60 | 10 | — | 90 | 90 | — | 90 | 100 | 100 |
| 72 | 125 | 10 | — | 90 | 70 | — | 95 | 100 | 100 |
| 76 | 60 | 0 | 30 | 95 | — | 95 | — | 100 | 95 |
| 77 | 60 | 0 | — | 95 | — | 90 | — | 100 | 90 |
| 80 | 125 | 0 | — | 95 | — | 90 | — | 100 | 95 |
| 81 | 60 | — | — | 100 | — | 95 | — | 100 | 100 |
| 82 | 60 | 0 | — | 60 | — | 90 | — | 100 | 100 |
| 84 | 125 | 5 | 30 | 95 | — | 90 | — | 95 | 100 |
| 85 | 125 | 60 | — | 95 | — | 95 | — | 100 | 100 |
| 86 | 125 | 10 | 40 | 80 | — | 70 | — | 100 | 95 |
| 89 | 125 | 0 | — | 100 | — | 90 | — | 100 | 100 |
| 93 | 60 | 0 | — | 90 | — | 80 | — | 95 | 90 |
| 108 | 125 | 5 | — | 90 | — | 95 | — | 95 | 90 |
| 121 | 500 | 10 | — | 70 | — | 80 | — | 90 | 95 |
| 129 | 250 | 10 | 10 | 95 | 95 | 90 | 60 | 90 | 95 |
| 130 | 250 | 10 | 0 | 95 | 95 | 80 | 95 | 95 | 95 |
| 131 | 250 | 0 | 0 | 95 | 90 | 90 | 95 | 80 | 95 |
| 134 | 500 | 0 | 20 | 95 | 90 | 70 | 80 | 90 | 95 |
| 135 | 125 | — | 40 | 95 | 95 | 90 | 90 | 90 | 95 |
| 136 | 125 | 30 | 20 | 95 | 95 | 90 | 80 | 90 | 95 |
| 140 | 30 | — | 10 | — | 95 | 95 | 80 | 80 | 95 |
| 141 | 15 | 30 | 0 | 90 | 80 | 80 | 90 | 80 | 90 |
| 142 | 15 | 20 | 10 | 95 | 80 | — | 80 | 80 | 80 |
| 143 | 60 | 20 | 0 | 90 | 90 | 90 | 80 | — | 90 |
| 144 | 125 | — | — | 90 | 90 | 95 | 80 | 95 | 95 |
| 145 | 60 | 0 | 0 | 95 | 95 | 95 | 95 | 60 | 95 |
| 3 | 60 | 10 | 20 | 90 | 70 | — | 80 | 95 | 80 |
| 146 | 60 | 0 | 10 | 80 | 90 | — | 80 | 80 | 90 |
| 147 | 15 | 30 | 0 | 95 | 90 | — | 70 | 70 | 80 |
| 148 | 60 | 40 | 0 | 80 | 95 | 90 | 80 | 80 | 95 |
| 149 | 125 | 0 | 30 | 95 | 95 | 80 | 95 | 95 | 95 |
| 150 | 125 | — | 10 | 80 | 90 | 80 | 70 | 80 | 80 |

TABLE A-continued

Pre-emergence test/Greenhouse

| Active compound of Preparation Example | Application rate (g of ai./ha) | Maize | Soya beans | Lo-lium | Poa | Sor-ghum | Ambro-sia | Matri-caria | Sola-num |
|---|---|---|---|---|---|---|---|---|---|
| 151 | 15 | 20 | 10 | 90 | 90 | 50 | 80 | 90 | 90 |
| 152 | 125 | — | 20 | 95 | 95 | 95 | 95 | 80 | 95 |
| 153 | 125 | 0 | 30 | — | 95 | — | 95 | 70 | 95 |
| 154 | 60 | 0 | 0 | 95 | 95 | 95 | 70 | 70 | 90 |
| 155 | 60 | — | 40 | 95 | 95 | 95 | 90 | 80 | 95 |
| 156 | 60 | 0 | 10 | 70 | 90 | 70 | 70 | 95 | 70 |
| 157 | 60 | 0 | 20 | 90 | 80 | 80 | 95 | 100 | 90 |
| 15g | 30 | 10 | — | 95 | 95 | 60 | 95 | 95 | 95 |
| 159 | 30 | 10 | — | 90 | 95 | 60 | 95 | 95 | 95 |
| 160 | 60 | 30 | 10 | 90 | 90 | 60 | 90 | 95 | 90 |
| 161 | 60 | 0 | 20 | 95 | 95 | — | 95 | 95 | 95 |
| 162 | 60 | — | 0 | 95 | 95 | 90 | 80 | 95 | 95 |
| 163 | 4 | 20 | 0 | 80 | 95 | 60 | 80 | — | 90 |
| 164 | 8 | 20 | 0 | 95 | 95 | 90 | 100 | 70 | 95 |
| 165 | 8 | 0 | 10 | — | 90 | 70 | 80 | 90 | 80 |
| 166 | 15 | 40 | — | 90 | 90 | 70 | 80 | 95 | 90 |
| 167 | 60 | — | 30 | 80 | 95 | 95 | 90 | 95 | 90 |
| 172 | 125 | — | 60 | 90 | 95 | 90 | 90 | 95 | 95 |

Example B
Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 2000 l of water/ha.

After three weeks, the degree of damage to the plants is rated in % damage in comparison to the development of the untreated control.

The figures denote:

0%=no action (like untreated control)

100%=total destruction

In this test, very strong activity against weeds is shown, for example, by the compounds of Preparation Examples 1, 5, 6, 7, 28, 30, 31, 32, 38, 44, 54, 63, 140, 141, 144, 151, 159, 162, 163, 164, 165 and 166, combined with predominantly good tolerance by crop plants such as, for example, maize.

TABLE B

Post-emergence test/greenhouse

| Active compound of Preparation Example | Application rate (g of ai./ha) | Maize | Digi-taria | Echi-no-chloa | Lo-lium | Sor-ghum | Ama-ran-thus | Gal-lium | Matri-caria | Stel-laria |
|---|---|---|---|---|---|---|---|---|---|---|
| 5 | 30 | 10 | 95 | 80 | 70 | 90 | 100 | — | 95 | 90 |
| 1 | 125 | 60 | 95 | 95 | 90 | 95 | 100 | — | 100 | 100 |
| 6 | 400 | 20 | 90 | 95 | 95 | 80 | 100 | 90 | 100 | 100 |
| 7 | 60 | 15 | 95 | 95 | 95 | 100 | — | 95 | 95 | 100 |
| 28 | 60 | 10 | 90 | 80 | 60 | 95 | 100 | 80 | 90 | 100 |
| 30 | 60 | 15 | 90 | 70 | 60 | 95 | 100 | 85 | 100 | 100 |
| 31 | 30 | 5 | 95 | 95 | 90 | 80 | 100 | 80 | 100 | 95 |
| 32 | 60 | 70 | 70 | 100 | 70 | 95 | 95 | 70 | 80 | 90 |
| 38 | 60 | 10 | 70 | 90 | — | 95 | 100 | — | 95 | 95 |
| 44 | 60 | 50 | 60 | 90 | 70 | 100 | 100 | 95 | 95 | — |
| 54 | 60 | 30 | — | 95 | 95 | 95 | 100 | 85 | 100 | 100 |
| 63 | 60 | — | 50 | 90 | 70 | 80 | 100 | 90 | 95 | 100 |
| 140 | 250 | — | 95 | 90 | — | 95 | 100 | 95 | 90 | 70 |
| 141 | 30 | 10 | 70 | 90 | — | 90 | 100 | 90 | 70 | 95 |
| 144 | 250 | — | 95 | 95 | 70 | 95 | 100 | 95 | 70 | 95 |
| 151 | 30 | 60 | 90 | 70 | 60 | 90 | 95 | 90 | 90 | 90 |
| 159 | 60 | — | 60 | 80 | 60 | 70 | 95 | 95 | 100 | 100 |
| 162 | 60 | — | 70 | 80 | 90 | 80 | — | — | 60 | 90 |
| 163 | 60 | 60 | 80 | 70 | 80 | 95 | 100 | 95 | 100 | 95 |
| 164 | 60 | — | 60 | 80 | 70 | 95 | 100 | 90 | 100 | 95 |
| 165 | 60 | — | 50 | 80 | 50 | 90 | 95 | 95 | 95 | 95 |
| 166 | 60 | — | 70 | 70 | 50 | 90 | 95 | 95 | 100 | 95 |

What is claimed is:

1. A sulphonamide of the formula (IIa):

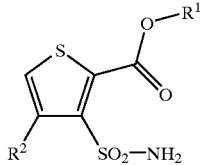

(IIa)

in which $R^1$ represents optionally cyano-, nitro-, halogen- or $C_1$–$C_4$-alkoxy-substituted $C_1$–$C_6$-alkyl, represents respectively optionally cyano- or halogen-substituted $C_2$–$C_6$-alkenyl or $C_2$–$C_6$-alkinyl, represents respectively optionally cyano-, halogen- or $C_1$–$C_4$-alkyl-substituted $C_3$–$C_6$-cycloalkyl, $C_3$–$C_6$-cycloalkyl-$C_1$–$C_4$-alkyl, and $R^2$ represents cyano, nitro, halogen, represents respectively optionally cyano-, halogen- or $C_1$–$C_4$-alkoxy-substituted $C_1$–$C_4$-alkyl, $C_1$–$C_4$-alkoxy, $C_1$–$C_4$-alkoxycarbonyl, or $C_1$–$C_4$-alkylsulphonyl, or represents respectively optionally cyano- or halogen-substituted $C_2$–$C_4$-alkenyl, $C_2$–$C_4$-alkinyl, $C_2$–$C_4$-alkenyloxy or $C_2$–$C_4$-alkinyloxy.

2. A sulphonyl iso(thio)cyanate of the formula (IV):

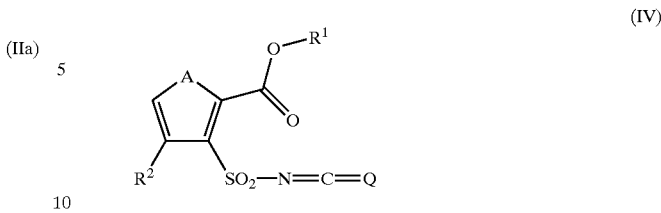

(IV)

in which

A represents sulphur;

Q represents oxygen or sulphur;

$R^1$ represents optionally cyano-, nitro-, halogen- or $C_1$–$C_4$-alkoxy-substituted $C_1$–$C_6$-alkyl, represents respectively optionally cyano- or halogen-substituted $C_2$–$C_6$-alkenyl or $C_2$–$C_6$-alkinyl, represents respectively optionally cyano-, halogen- or $C_1$–$C_4$-alkyl-substituted $C_3$–$C_6$-cycloalkyl, $C_3$–$C_6$-cycloalkyl-$C_1$–$C_4$-alkyl, and $R^2$ represents cyano, nitro, halogen, represents respectively optionally cyano-, halogen- or $C_1$–$C_4$-alkoxy-substituted $C_1$–$C_4$-alkyl, $C_1$–$C_4$-alkoxy, $C_1$–$C_4$-alkoxycarbonyl, $C_1$–$C_4$-alkylthio, $C_1$–$C_4$-alkylsulphinyl or $C_1$–$C_4$-alkylsulphonyl, or represents respectively optionally cyano- or halogen-substituted $C_2$–$C_4$-alkenyl, $C_2$–$C_4$-alkinyl, $C_2$–$C_4$-alkenyloxy or $C_2$–$C_4$-alkinyloxy.

* * * * *